US011020472B2

(12) United States Patent
Sato et al.

(10) Patent No.: US 11,020,472 B2
(45) Date of Patent: *Jun. 1, 2021

(54) MULTIVALENT RECOMBINANT SPV

(71) Applicant: CEVA SANTE ANIMALE, Libourne (FR)

(72) Inventors: Takanori Sato, Kanagawa (JP); Shuji Saitoh, Yokohama (JP); Yasutoshi Komiya, Yokohama (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/307,954

(22) PCT Filed: Jun. 9, 2017

(86) PCT No.: PCT/EP2017/064183
§ 371 (c)(1),
(2) Date: Dec. 7, 2018

(87) PCT Pub. No.: WO2017/212048
PCT Pub. Date: Dec. 14, 2017

(65) Prior Publication Data
US 2019/0307876 A1    Oct. 10, 2019

(30) Foreign Application Priority Data

Jun. 10, 2016  (EP) .................... 16305697

(51) Int. Cl.
| A61K 39/12 | (2006.01) |
|---|---|
| A61P 31/20 | (2006.01) |
| C12N 15/86 | (2006.01) |
| A61K 39/00 | (2006.01) |

(52) U.S. Cl.
CPC .............. *A61K 39/12* (2013.01); *A61P 31/20* (2018.01); *C12N 15/86* (2013.01); *A61K 2039/5254* (2013.01); *A61K 2039/5256* (2013.01); *A61K 2039/552* (2013.01); *C12N 2710/24034* (2013.01); *C12N 2710/24043* (2013.01); *C12N 2750/10034* (2013.01)

(58) Field of Classification Search
None
See application file for complete search history.

(56) References Cited

U.S. PATENT DOCUMENTS

| 8,703,468 | B2 | 4/2014 | Penzes et al. |
|---|---|---|---|
| 10,106,819 | B2 | 10/2018 | Sato |
| 10,174,084 | B2 | 1/2019 | Sato |
| 2010/0150959 | A1 | 6/2010 | Sheppard et al. |
| 2016/0046676 | A1 | 2/2016 | Sato |
| 2017/0335343 | A1* | 11/2017 | Sato ........................ C12N 15/86 |

FOREIGN PATENT DOCUMENTS

| EP | 2 564 869 | 3/2013 |
|---|---|---|
| WO | WO 99/29717 | 6/1999 |
| WO | WO 2008/140414 | 11/2008 |
| WO | WO 2010/068969 | 6/2010 |
| WO | WO 2014/167060 | 10/2014 |
| WO | WO 2015/027163 | 2/2015 |
| WO | WO 2016/097281 | 6/2016 |

OTHER PUBLICATIONS

Falivene, J. et al. "Improving the MVA Vaccine Potential by Deleting the Viral Gene Coding for the IL-18 Binding Protein" *PLOS ONE*, Feb. 22, 2012, pp. 1-15, vol. 7, Issue 2, e32220.
Written Opinion in International Application No. PCT/EP2017/064183, dated Aug. 9, 2017, pp. 1-6.
Allowed claims of U.S. Appl. No. 14/783,117, 2018, pp. 1-2.
Kwak, H. et al. "Improved protection conferred by vaccination with a recombinant vaccinia virus that incorporates a foreign antigen into the extracellular enveloped virion" *Virology*, May 1, 2004, pp. 337-348, vol. 322.
Katz, E. et al. "The Cytoplasmic and Transmembrane Domains of the Vaccinia Virus B5R Protein Target a Chimeric Human Immunodeficiency Virus Type 1 Glycoprotein to the Outer Envelope of Nascent Vaccinia Virions" *Journal of Virology*, Apr. 1997, pp. 3178-3187, vol. 71, No. 4.
Katz, E. et al. "Immunogenicity of Recombinant Vaccinia Viruses that Display the HIV Type 1 Envelope Glycoprotein on the Surface of Infectious Virions" *AIDS Research and Human Retroviruses*, Nov. 20, 1997, pp. 1497-1500, vol. 13, No. 17.
Ward, B. et al. "Visualization of Intracellular Movement of Vaccinia Virus Virions Containing a Green Fluorescent Protein-B5R Membrane Protein Chimera" *Journal of Virology*, May 1, 2001, pp. 4802-4813, vol. 75, No. 10.
Lin, H. et al. "Construction and immunogenicity of recombinant swinepox virus expressing capsid protein of PCV2" *Vaccine*, Sep. 1, 2012, pp. 6307-6313, vol. 30, No. 44.
Written Opinion in International Application No. PCT/EP2014/057287, dated Aug. 6, 2014, pp. 1-6.
Isaacs, S. N. et al. "Characterization of a Vaccinia Virus-Encoded 42-Kilodalton Class I Membrane Glycoprotein Component of the Extracellular Virus Envelope" *Journal of Virology*, Dec. 1992, pp. 7217-7224, vol. 66, No. 12.

(Continued)

*Primary Examiner* — Benjamin P Blumel
(74) *Attorney, Agent, or Firm* — Saliwanchik, Lloyd & Eisenschenk

(57) ABSTRACT

The present invention relates to novel recombinant swinepox viruses and their use in vaccine compositions. The recombinant swinepox viruses of the invention are doubly defective for IL18bp and TK genes, and comprise at least one foreign gene cloned into defective TK gene sequence. The invention is particularly suited to produce swine vaccines, particularly for vaccinating swine against PCV2 infection.

22 Claims, 11 Drawing Sheets

Figure 2:
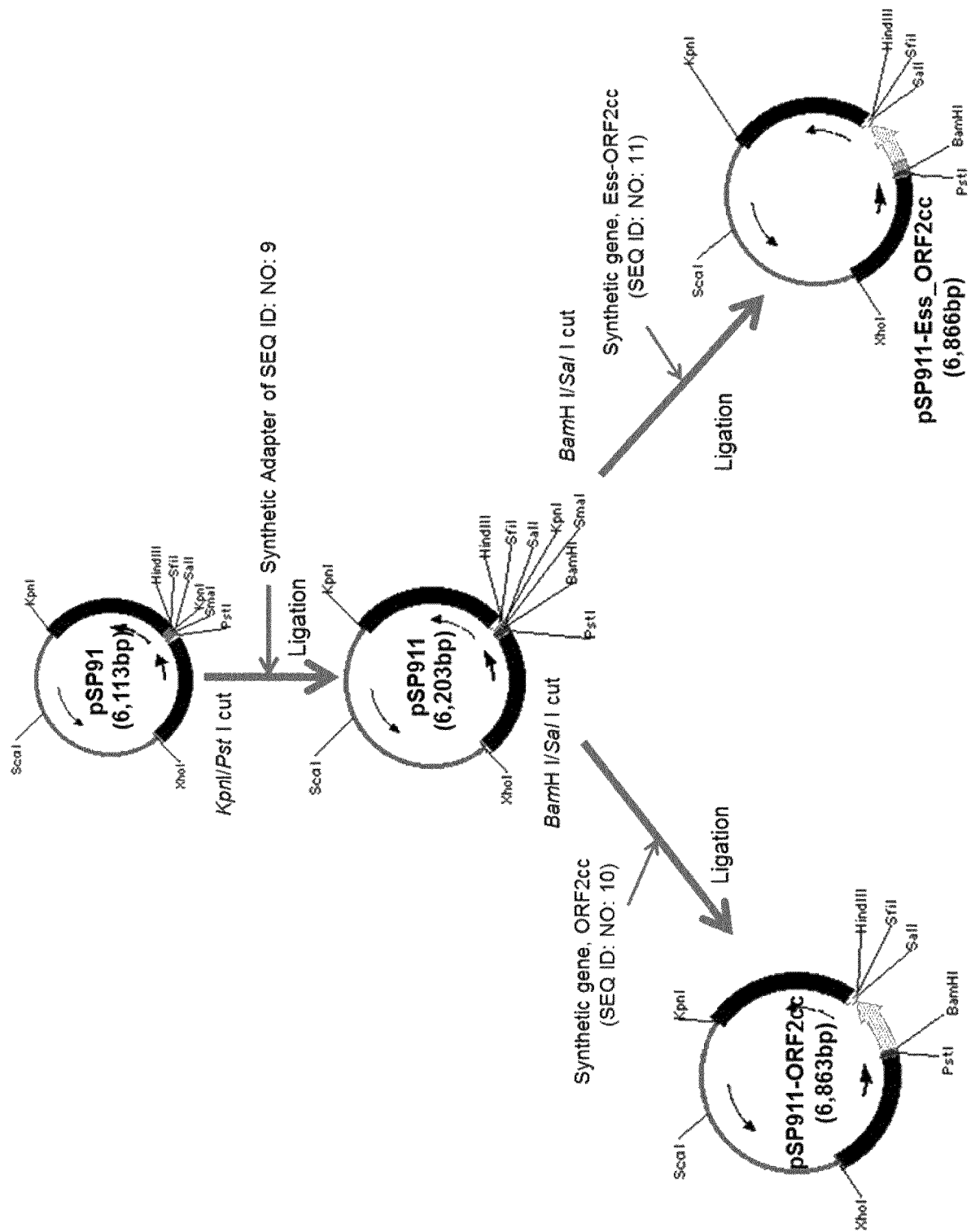

Specification includes a Sequence Listing.

(56) References Cited

OTHER PUBLICATIONS

Nawagitgul, P. et al. "Open reading frame 2 of porcine circovirus type 2 encodes a major capsid protein" *Journal of General Virology*, 2000, pp. 2281-2287, vol. 81.

De Boisseson, C. et al. "Molecular characterization of *Porcine circovirus* type 2 isolates from post-weaning multisystemic wasting syndrome-affected and nonaffected pigs" *Journal of General Virology*, 2004, pp. 293-304, vol. 85.

Misinzo, G. et al. "Inhibition of Endosome-Lysosome System Acidification Enhances Porcine Circovirus 2 Infection of Porcine Epithelial Cells" *Journal of Virology*, Feb. 2008, pp. 1128-1135, vol. 82, No. 3.

Roca, M. et al. "In vitro and in vivo characterization of an infectious clone of a European strain of porcine circovirus type 2" *Journal of General Virology*, 2004, pp. 1259-1266, vol. 85.

Database EMBL EMBO; Accession No. AY321993, "Porcine circovirus 2 strain Fh16", Jul. 15, 2003, pp. 1-2.

Database EMBL EMBO; Accession No. AAX83756, "Porcine circovirus type II B9 nucleotide sequence fragment #1", Aug. 27, 1999, p. 1.

Written Opinion in International Application No. PCT/EP2009/066007, dated Mar. 15, 2010, pp. 1-7.

Blanchard, P. et al. "Protection of swine against post-weaning multisystemic wasting syndrome (PMWS) by porcine circovirus type 2 (PCV2) proteins" *Vaccine*, 2003, pp. 4565-4575, vol. 21.

\* cited by examiner

MULTIVALENT RECOMBINANT SPV

CROSS-REFERENCE TO RELATED APPLICATION

This application is the U.S. national stage application of International Patent Application No. PCT/EP2017/064183, filed Jun. 9, 2017.

The Sequence Listing for this application is labeled "Seq-List.txt" which was created on Nov. 30, 2018 and is 8 KB. The entire content of the sequence listing is incorporated herein by reference in its entirety.

The present invention relates to novel recombinant swinepox viruses and their use in vaccine compositions. The recombinant swinepox viruses of the invention are doubly-defective and allow effective expression of one or more foreign gene sequences in vivo. The invention is particularly suited to produce swine vaccines, particularly for vaccinating swine against PCV2 infection.

BACKGROUND

Different types of viruses have been proposed in the art as vector for gene delivery or peptide expression in vivo. In particular, veterinary vaccines have been prepared that express at least one relevant antigen using recombinant viruses such as poxviruses (Ogawa R. et al., Vaccine, 8:486-490 (1990)), adenoviruses (HSU, K. H. et al., Vaccine, 12; 607-612 (1994)), baculoviruses, as well as herpesviruses (Shin, M.-F. et al., Proc. Natl. Acad. Sci. U.S.A., 81:5867-5870 (1984)). Examples of specific virus vectors that permit the expression of a gene for a foreign antigen include Aujeszky's disease virus (pseudorabies virus; PRV) (Van Zijl M. et al., J. Virol., 65:2761-2765 (1991)), herpesvirus of turkey (HVT) (Morgan R. W. et al., Avian Dis. 36:858-870 (1992)), and Marek's disease virus (MDV). Recombinant vectors based on the genus herpesvirus are under intensive study.

There is, however, a need in the art for new viral vector products that can be used to express recombinant peptides or proteins in vivo. In this regard, poxviruses have been engineered to encode different polypeptides. Poxviruses, once released into the blood from infected cells, can infect other cells and thereby potentially lead to elevated expression levels. Recombinant poxviruses have been produced from different types of poxviruses, including cowpox virus, vaccinia virus, and swinepox virus (SPV). So far, however, SPV recombinants have been produced essentially by cloning foreign gene sequences in a genetic region that is considered non-essential for survival of SPV, the TK region (Richard W. Moyer, Eladio Vinuela, E. P. J. Gibbs, U.S. Pat. No. 5,651,972 (1997)).

PCT/EP2015/080468, by applicant, describes the IL-18 binding protein (IL18bp) gene sequence as a novel and very advantageous cloning site in SPV.

Continuing their research, the inventors of the present invention have now found that doubly-defective SPVs, wherein both IL18bp gene and at least the TK or ARP gene are defective, allow efficient and stable expression of several foreign gene sequences in vivo, can be effectively propagated in culture, and are highly attenuated in vivo. These doubly-defective SPVs thus exhibit improved properties and can be used to produce therapeutics or vaccines for treatment of any mammal, particularly swine.

SUMMARY OF THE INVENTION

The present invention relates to novel recombinant swinepox viruses and their use for gene delivery and expression in vivo, particularly in vaccine compositions. The recombinant swinepox viruses of the invention are doubly-defective for both the IL18bp gene and the TK and/or ARP gene. Preferably the SPVs of the invention contain one or more foreign gene sequences, preferably cloned into the defective TK, ARP, or IL18bp gene regions of swinepox virus. The invention is particularly suited to produce swine vaccines, particularly for vaccinating swine against PCV2 infection.

A first object of the present invention thus relates to a recombinant swinepox virus (rSPV) having at least a first and a second defective viral genes, wherein the first defective viral gene is IL18bp gene and the second defective viral gene is the Thymidine Kinase (TK) or Ankirin Repeat Protein (ARP) gene.

In a particular embodiment, the invention provides a recombinant swinepox virus (SPV) comprising a defective IL18bp gene and a defective TK gene.

In another particular embodiment, the invention provides a recombinant swinepox virus (SPV) comprising a defective IL18bp gene and a defective ARP gene.

Preferably, the rSPV comprises a deletion of at least 50 pb, at least 100 pb, at least 200 pb or even at least 300 pb in each of the target defective viral gene sequences. Furthermore, in a preferred embodiment, the rSPV further comprises at least one first foreign gene sequence, which may be placed at any location in the rSPV, preferably in replacement of all or part of the deleted viral gene sequence. In a particular embodiment, the rSPV of the invention comprises two foreign gene sequences, a first inserted in place of the deleted viral IL18bp gene sequence and a second inserted in place of the deleted viral TK or ARP gene sequence.

A further object of the invention resides in a nucleic acid molecule comprising the genome of a rSPV as defined above.

A further object of the invention is a host cell comprising a rSPV or a nucleic acid molecule of the invention.

The present invention further provides a method for producing a rSPV, comprising infecting or introducing into a competent cell a nucleic acid molecule as defined above and collecting the rSPV.

The invention also relates to a method for propagating a rSPV, comprising infecting a competent cell a rSPV as defined above and collecting the rSPV produced by said cells.

The invention also concerns a composition, preferably a veterinary composition, comprising a rSPV as defined above, or a cell as defined above, or a nucleic acid molecule as defined above, and an excipient.

A further object of the invention is a vaccine composition comprising a rSPV as defined above, or a cell as defined above, or a nucleic acid molecule as defined above, a suitable excipient and, optionally, an adjuvant.

The invention also relates to a rSPV or cell or nucleic acid molecule as defined above for use for delivering a therapeutic or vaccinating peptide or protein to a porcine.

The invention also relates to a rSPV or cell or nucleic acid molecule as defined above for use for immunizing or vaccinating a mammal, preferably a porcine against a pathogen.

The invention also relates to a method for vaccinating a mammal, preferably a porcine, against a pathogen, comprising administering to the mammal a rSPV or cell or nucleic acid molecule as defined above.

The invention also concerns a vaccination kit for immunizing a porcine which comprises the following components:

a. an effective amount of a rSPV or vaccine as defined above, and
b. a means for administering said rSPV or vaccine to said porcine.

The invention may be used to deliver and express any foreign gene sequence to a mammal, particularly a porcine. It is particularly suited for expressing foreign antigens to immunize or vaccinate porcine (e.g., pigs, piglets, sow).

LEGEND TO THE FIGURES

Figure 1:
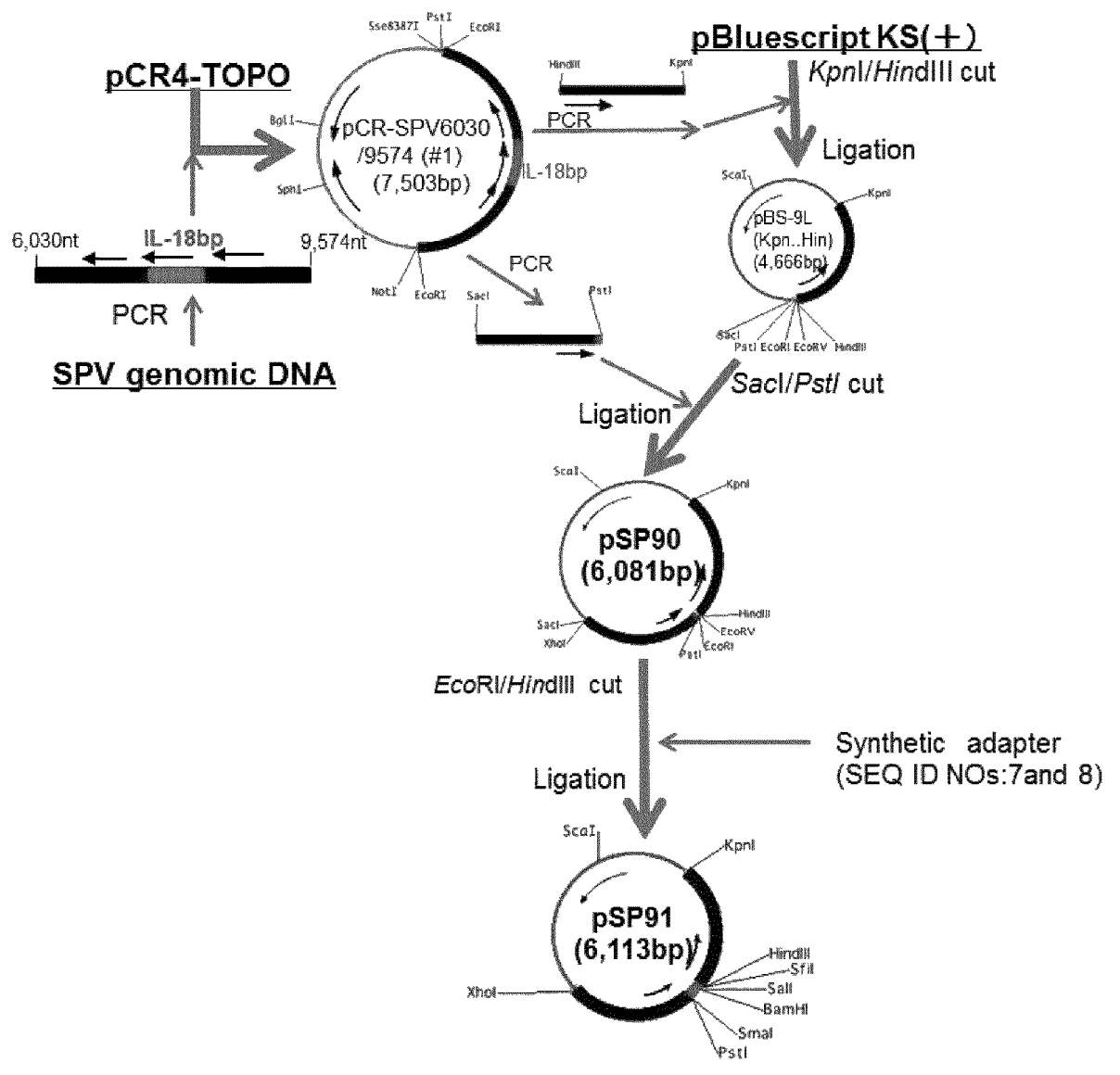

FIG. 1. Construction scheme of the intermediate plasmid, Ps-91.

FIG. 2. Construction scheme of the homologous plasmids, pSP911-Ess_ORF2cc and pSP911-ORF2cc.

Figure 3:
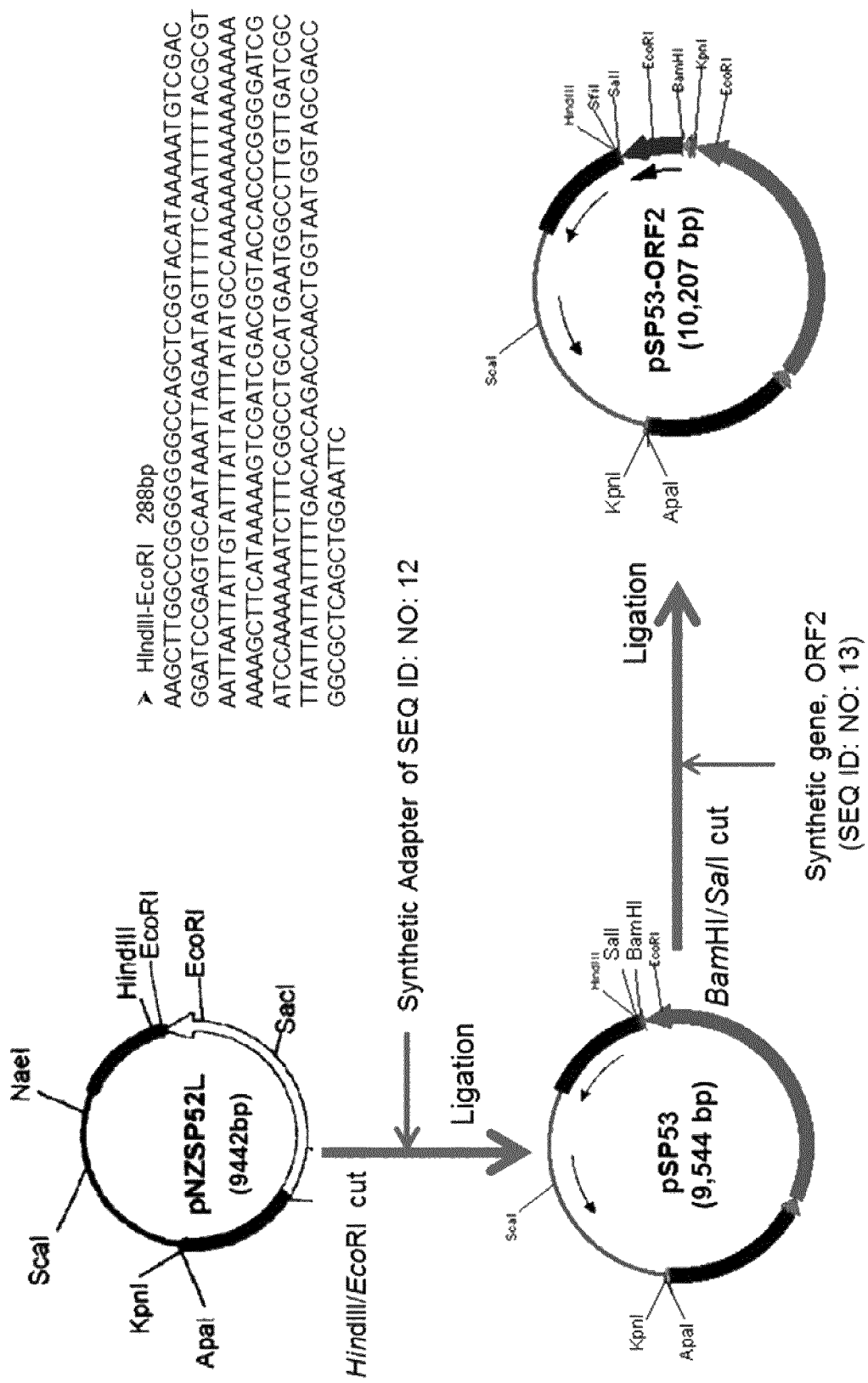

FIG. 3. Construction scheme of the homologous plasmid, pSP53-ORF2.

Figure 4:
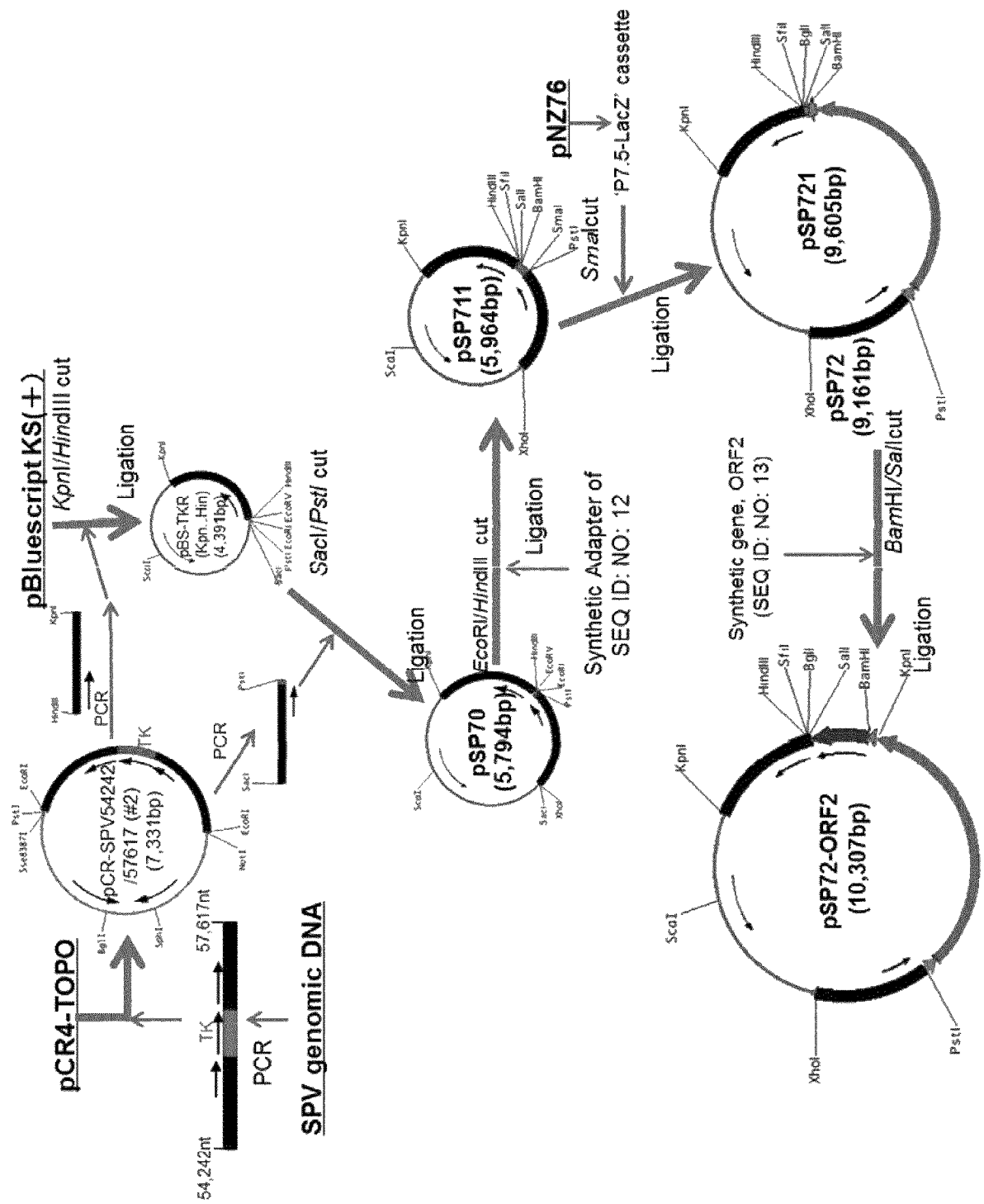

FIG. 4. Construction scheme of the homologous plasmid, pSP72-ORF2.

Figure 5:
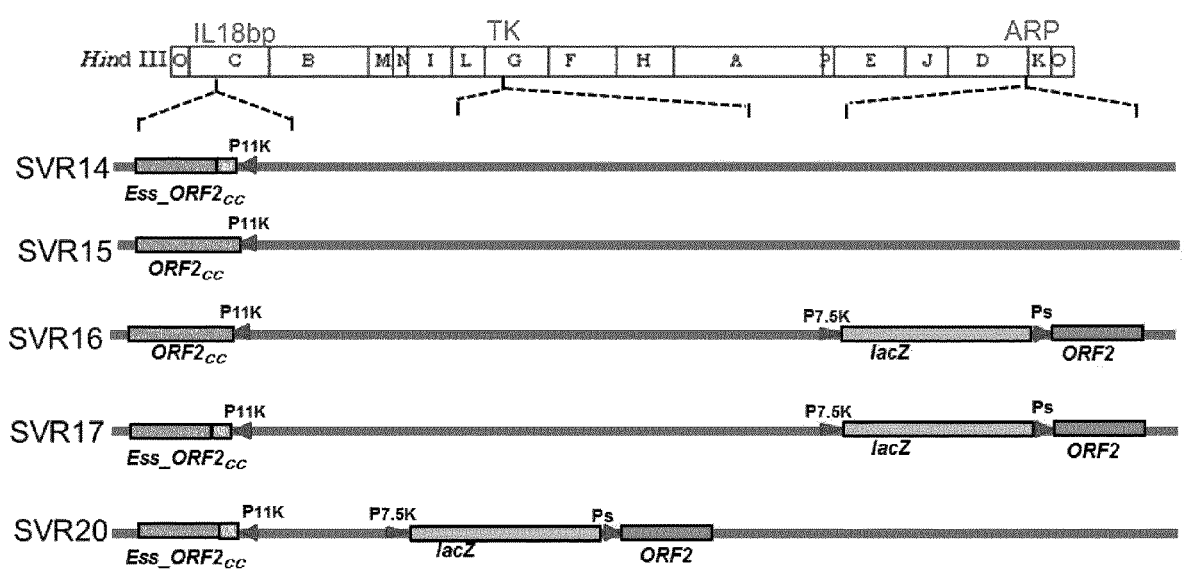

FIG. 5. Illustration of genome structures of recombinant SPVs.

Figure 6:
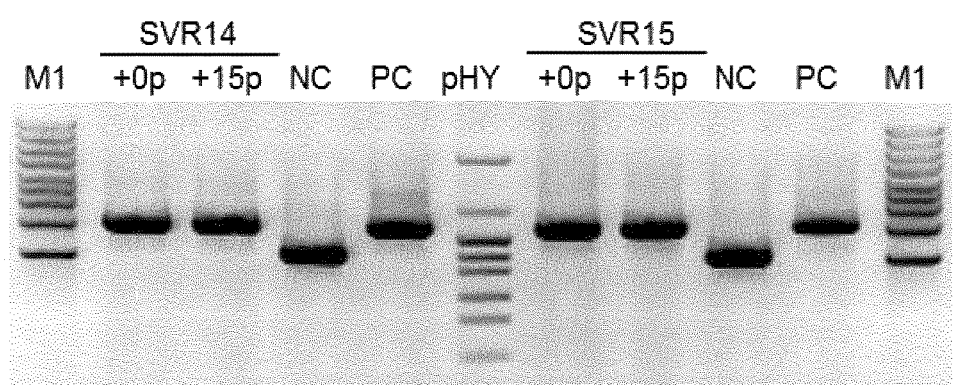
Figure 6:
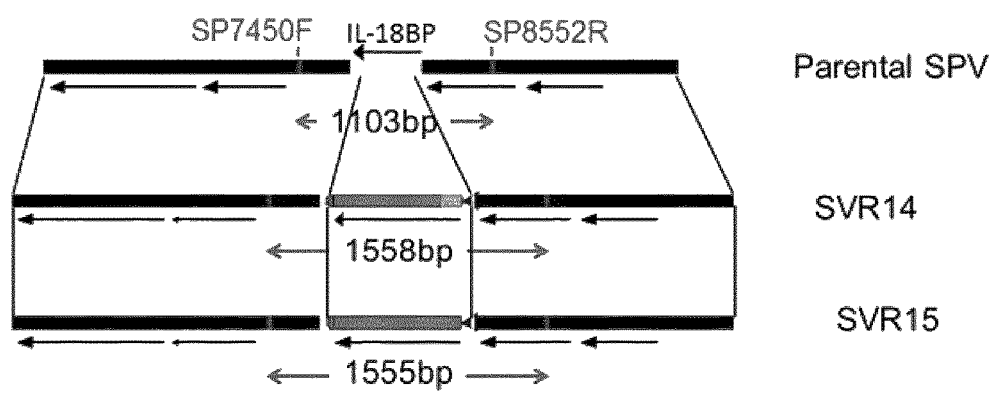

FIG. 6 PCR check of SRV14 and SRV15 in vitro passage.
(A) PCR results. PCR was conducted using a primer set of SP7450F and SP8552R. Each template was virus DNA of in vitro passage +0 or +15p of SVR14 and SVR15. Each transfer plasmid at transfection for making SVR12, SVR14 or SVR15, and pCR4-SPV6030/9574 was used for a template of positive control (PC) or negative control (NC), respectively. Molecular weight markers were 10 kb (M1) and pHY. (B) Illustration of the IL-18bp gene franking region of parent and rSPVs, SVR14 and SVR15. Yellow box is the IL-18bp gene.

Figure 7:
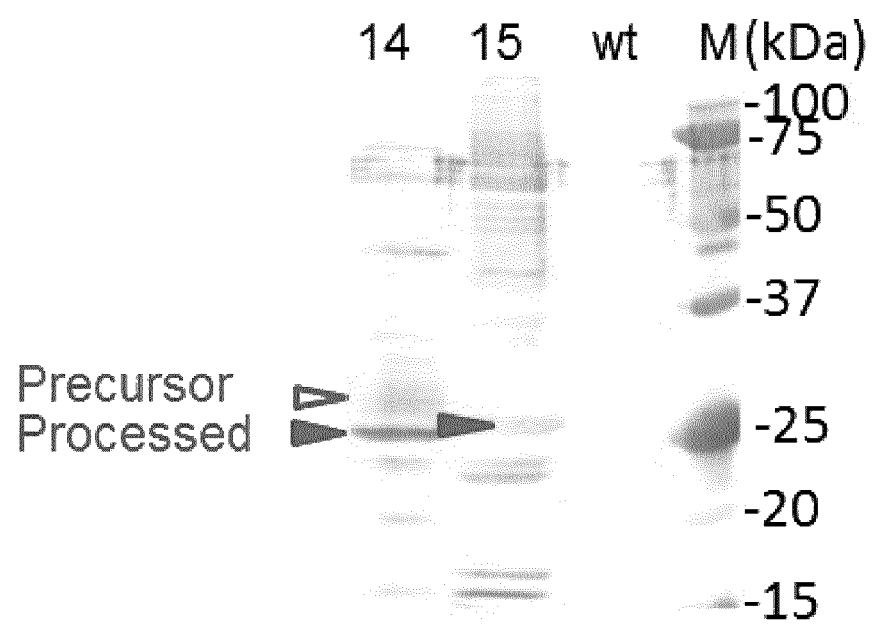

FIG. 7. Western blotting of purified rSPVs.
ESK-4 cells were infected with wild-type SPV (wt), SVR14 (14), or SVR15 (15). Six days later, cell lysates were applied to 15% SDS-PAGE and western blot analysis using rat anti-ORF2 (1:500), biotin conjugated goat anti-rat IgG secondary (1:1000), and ABC-ALP (Vecterstain). M: Molecular weight marker.

Figure 8:
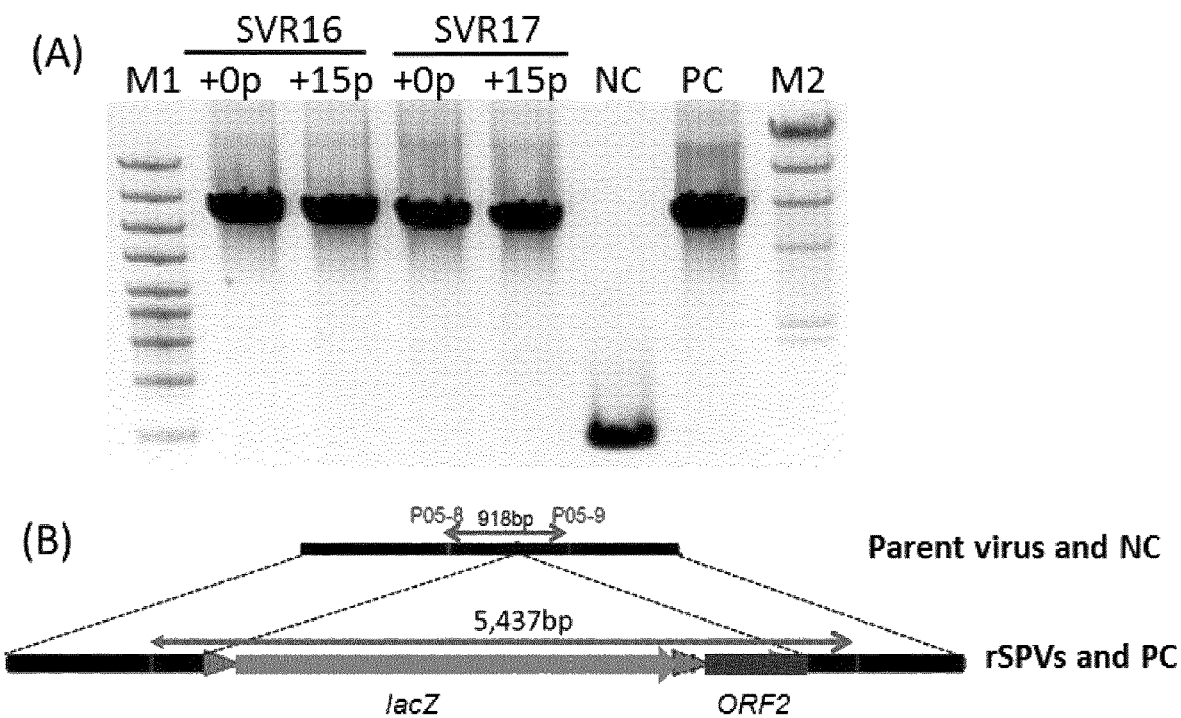

FIG. 8. PCR check of SVR16 and 17 in vitro passage.
(A) PCR results. PCR was conducted using a primer set of P05-8 and P05-9. Each template was virus DNA of SVR16 and 17 in vitro passages (+0p and +15p). The transfer plasmid, pSP53-ORF2 and pNZSP5 (described in Experiment 3 and FIG. 3 of JP2003-111591A) were used as positive control (PC) and negative control (NC) templates, respectively. Molecular weight markers were 10 kb (M1) and λ HindIII (M2). (B) Illustration of ARP gene franking region of parent and rSPVs, SVR16 and SVR17.

Figure 9:
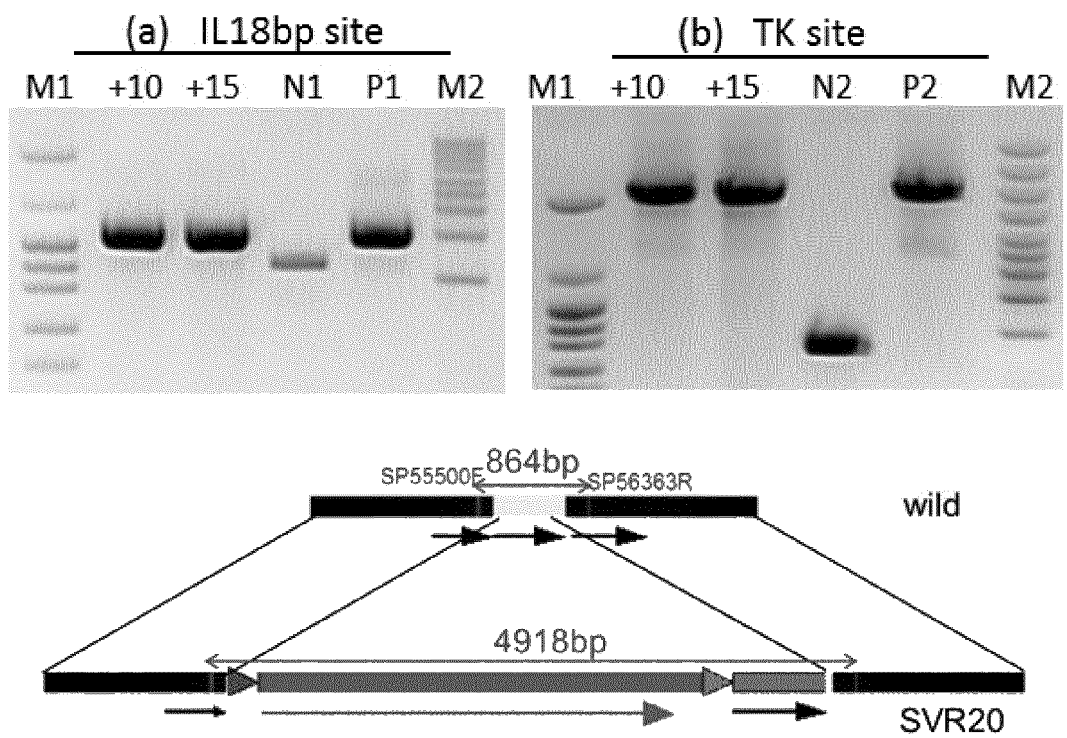

FIG. 9. PCR check of SVR20 in vitro passage.
(A) PCR results. PCR was conducted using two primer sets of (a) SP7450F and SP8552R, and (b) SP55500F and SP56363R. Each template was each virus DNA of SVR20+0p or +15p. Each plasmid, pCR4-SPV6030/9574 (N1), or pCR4-SPV54242/57617 (N2), and pSP911-ORF2cc (P1) or pSP72-ORF2 (P2) was used for templates for negative and positive control. PCR products of (a) or (b) were set on 2% or 0.8% agarose gel, respectively. Molecular weight markers were 10 kb (M1) and pHY (M2) markers. (B) Illustration of TK gene franking region of wild-type SPV and SVR20. Yellow box is the TK gene.

Figure 10:
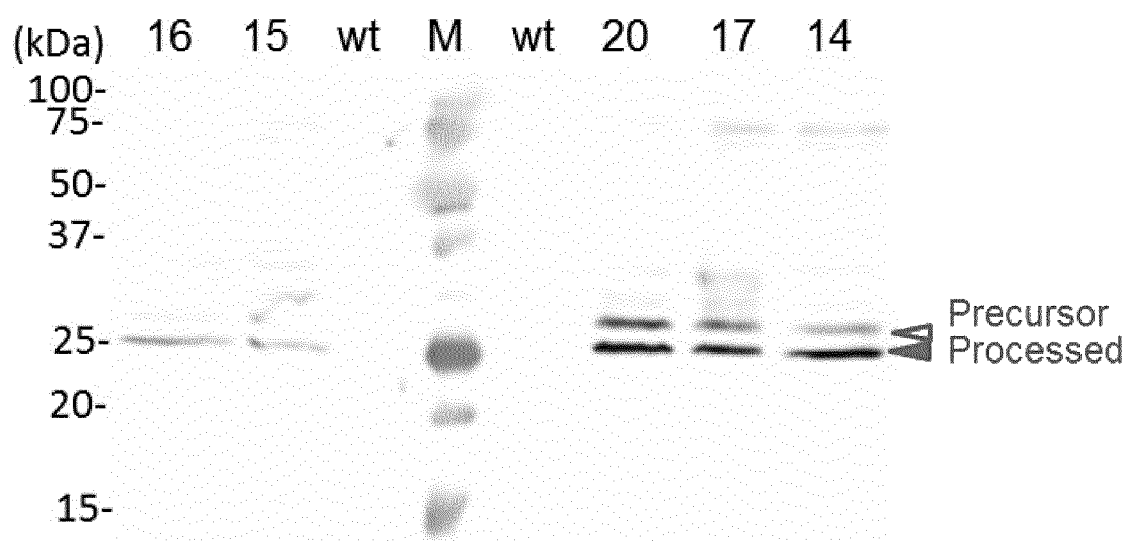

FIG. 10. Western blotting of purified rSPVs
ESK-4 cells were infected with wild-type SPV (wt), SVR14 (14), SVR15 (15), SVR16 (16), SVR17 (17), or SVR20 (20) at M.O.I. of 0.1. Six days later, cell lysates were applied to 15% SDS-PAGE and western blot analysis using rat anti-ORF2 (1:500), biotin conjugated goat anti-rat IgG secondary (1:1000), and ABC-ALP (Vecterstain). M: Molecular weight marker.

Figure 11:
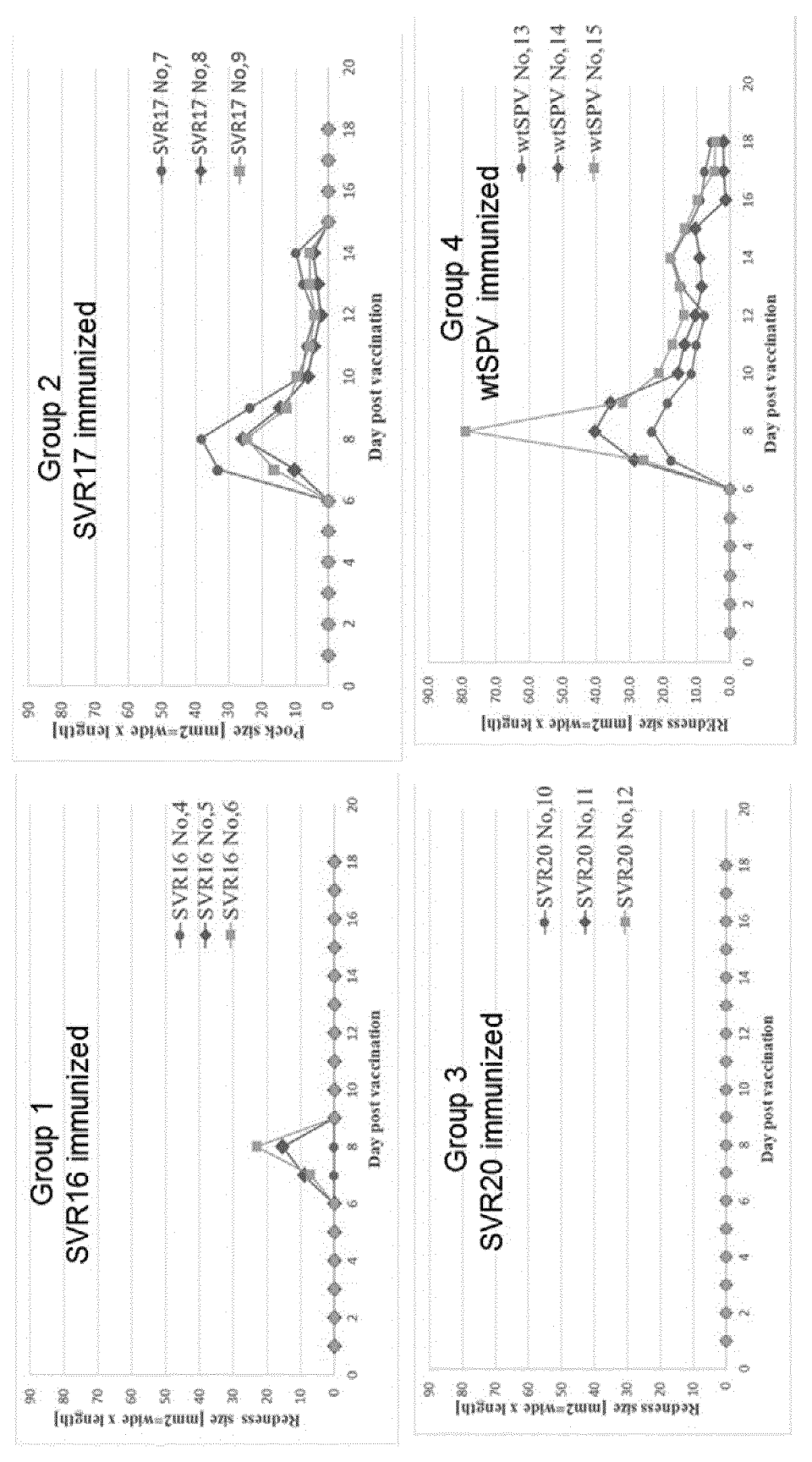

FIG. 11. Transition of redness sizes at injection sites of pigs.

DETAILED DESCRIPTION OF THE INVENTION

The present invention relates to novel recombinant swinepox viruses and the uses thereof. The recombinant swinepox viruses of the invention are doubly defective for IL18bp gene and for a second gene selected from TK and ARP genes of swinepox virus, and preferably contain one or more foreign gene sequences. As shown in the experimental section, such double-defective SPV vectors allow sustained and efficient gene expression. Furthermore, the rSPVs of the invention are stable and can produce improved immune responses in vivo. Moreover, these SPV vectors of the invention are highly attenuated. This is the first report of a doubly defective SPV virus and the first demonstration that such SPVs can express foreign gene sequences, resulting in stable, immunogenic and highly-producing recombinant SPV vectors. The rSPV of the invention may contain more than one foreign gene sequences, and they may be used alone or in combination with other recombinant viruses or antigens to generate improved vaccines. The invention is particularly suited to produce swine vaccines, particularly for vaccinating swine against PCV2 infection.

rSPVs

Within the context of the invention, a recombinant swinepox virus designates, generally, a swinepox virus having an artificially (e.g., recombinantly) engineered genome. rSPV include, particularly, swinepox viruses containing foreign genetic material or sequence in their genome. rSPV typically comprise a SPV genome containing a foreign genetic sequence, packaged into a SPV capsid or envelop, which may also contain a foreign protein or peptide.

rSPV of the present invention may be prepared starting from any SPV, such as any naturally occurring SPVs or any SPVs available from collections such as ATCC, CNCM, etc. Preferably, the rSPV of the invention are produced from SPV kasza strain (VR-363), isolate 17077-99 (GeneBank Acc: AF410153.1), or strain VTCC/AVA/121 (GeneBank Acc: KJ725378.1). Such SPVs are available from collections or libraries, or may be cloned from their publicly available genomic sequences. Further SPV isolates may also be isolated from infected animals and used to prepare rSPV of the invention.

SPV or rSPV may be cultured or maintained or propagated in any suitable cell. For instance, SPVs may be cultured, maintained or propagated in embryonic swine kidney cells, such as ESK-4 cells (CL-184), routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028).

In order to construct a recombinant virus of the present invention, initially, the SPV virus may be propagated in a suitable host cell and then the genomic DNA obtained. Subsequently, the IL18bp, TK and/or ARP regions of the genomic DNA are identified and rendered defective (e.g., deleted, in all or in part). Subsequently, or simultaneously, a foreign gene sequence (or a cloning site allowing insertion of a foreign gene sequence) may be inserted into the genomic DNA, optionally in place of the deleted endogenous gene sequence. The recombinant SPV genome thus obtained may be used to produce rSPV by transformation of suitable competent cells according to conventional techniques. Alternatively, a shuttle vector may be produced containing a foreign gene sequence (or a cloning site) flanked by sequences homologous to IL18bp, TK and/or ARP gene regions and located in the coding region. Upon introduction into a competent cell in the presence of a SPV virus or genome, homologous recombination between the shuttle vector and the genome generates the rSPV having defective genes and containing a foreign gene sequence. Once a rSPV has been engineered as described above, it can be easily replicated and propagated by simple culture on any competent cells.

SPVs may be cultured, maintained or propagated in embryonic swine kidney cells, such as ESK-4 cells (CL-184), routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028). DNA can be extracted from virus-infected cells according to any conventional method. For instance, cells grown in monolayers can be scraped and then spun to harvest the supernatant. After protein is denatured in a lysis buffer and removed, DNA can be extracted with phenol and/or ethanol.

Within the context of the invention, a "defective" gene means a partially or fully deleted gene. More particularly, a SPV containing a defective gene is a SPV containing a deletion of at least 20 bp within a coding sequence of said gene, preferably at least 50 bp, even more preferably at least 100 bp, further more preferably at least 150 bp, at least 200 bp, or even at least 300 bp.

The IL18bp gene of a viral SPV DNA contains approximately 402 bp, and is generally located at nt residues 7745-8146 of a SPV genome. As a specific example, in SPV kasza strain (VR-363), the IL18bp gene is located at nt7745-8146. The exact position of the IL18bp gene in any strain of SPV may be identified easily using common knowledge, routine sequence analysis and/or sequence alignment.

The TK gene of a viral SPV DNA contains approximately 543 bp, and is generally located at nt residues 55625-56167 of a SPV genome. As a specific example, in SPV kasza strain (VR-363), the TK gene is located at nt55625-56167. The exact position of the IL18bp gene in any strains of SPV may be identified easily using common knowledge, routine sequence analysis and/or sequence alignment.

The ARP gene of a viral SPV DNA contains approximately 1455 bp, and is generally located at nt residues 137100-138554 of a SPV genome. As a specific example, in SPV kasza strain (VR-363), the ARP gene is located at nt137100-138554. The exact position of the IL18bp gene in any strains of SPV may be identified easily using common knowledge, routine sequence analysis and/or sequence alignment.

Preferred rSPVs of the invention comprise a defective IL18bp gene, wherein the endogenous IL18bp gene lacks at least 50 nt, preferably at least 100 nt, even more preferably at least 150 nt, at least 200 nt, at least 250 nt, at least 300 nt, further more preferably between 320 nt and 380 nt. Specific and preferred rSPVs of the invention contain a deletion of at least nt 100-200 of IL18bp gene, even more preferably of at least nt50-300 of IL18bp gene, such as nt31-382 or nt19-369 of IL18bp gene.

Preferred rSPVs of the invention further comprise a defective TK gene, wherein the endogenous TK gene lacks at least 50 nt, preferably at least 100 nt, even more preferably at least 150 nt, at least 200 nt, at least 250 nt, at least 300 nt, further more preferably at least 400 nt, such as between 420 nt and 500 nt. Specific and preferred rSPVs of the invention contain a deletion of at least nt 100-300 of TK gene, even more preferably of at least nt70-450 of TK gene, even more preferably of at least nt60-500 of the TK gene, such as nt59-536 of the TK gene.

As regards the ARP gene, in rSPVs of the invention comprising a defective ARP gene, the endogenous ARP gene coding sequence preferably lacks at least 50 nt, preferably at least 100 nt, even more preferably at least 110 nt. Specific and preferred rSPVs of the invention contain a deletion of at least nt1150-1200 of ARP gene, even more preferably of at least nt1130-1220 of ARP gene, even more preferably of at least nt1116-1228 of the ARP gene. Larger deletions may also be performed, covering between 800 and 1300 bp of the ARP gene.

In a particular embodiment, the rSPVs of the invention contains a deletion of at least nt50-300 of IL18bp gene and a deletion of at least nt70-450 of TK gene. In a specific embodiment, the rSPV contains a deletion of nt31-382 or nt19-369 of IL18bp gene and a deletion of nt59-536 of the TK gene.

In another particular embodiment, the rSPVs of the invention contains a deletion of at least nt50-300 of IL18bp gene and a deletion of at least nt11340-1220 of ARP gene. In a specific embodiment, the rSPV contains a deletion of nt31-382 or nt19-369 of IL18bp gene and a deletion of nt1116-1228 of the TK gene.

In a particular embodiment, the rSPV of the invention comprises one foreign gene sequence inserted in place of one of the above deleted regions. In another embodiment, the rSPV comprises at least 2 foreign nucleic acids each located in a distinct place selected from the above deleted regions.

The construction of a rSPV of the invention may be carried out using methods known per se in the art, following guidance and information contained in the present application. In particular, the skilled artisan can insert a foreign gene sequence in the TK, ARP or IL18bp sequence, in replacement or all or part of the endogenous sequence, by using known methods such as mutagenesis, PCR, homologous recombination, etc.

In a particular embodiment, a shuttle vector is prepared by recombinant DNA technology in which a foreign gene sequence is cloned flanked by two IL18bp or TK homology regions. The homology regions typically contain each between 50-1000 nt of IL18bp or TK gene sequence, allowing specific homologous recombination. The shuttle vector may be prepared from any known or conventional plasmids, cosmids, phages, and the like, such as pBS plasmids, pBR322, pUC18, pUC19 and pHC79. The shuttle plasmid may then be introduced into an SPV-infected cell using known techniques such as electroporation, calcium phosphate, a lipofectin-based method, or the like. Recombinant SPV viruses having integrated the foreign gene sequence are then selected. Their sequence can be verified. The rSPV can then be maintained in any suitable competent cell. The virus can be maintained in culture, or purified and frozen or lyophilized.

Particular examples of rSPVs of the invention comprise a deletion of at least 50 nt in the IL18bp gene, and of at least 50 nt in the TK or ARP gene.

A preferred virus of the invention comprises a deletion of at least 100 nt in the IL18bp gene, and of at least 100 nt in the TK or ARP gene.

A more preferred virus of the invention comprises a deletion of at least 200 nt in the IL18bp gene, and of at least 200 nt in the TK gene.

Another particular virus of the invention is a recombinant swinepox virus (rSPV) having a defective viral IL18bp gene and containing no coding foreign gene sequence. Such virus is attenuated and may be used to produce rSPVs containing a foreign gene sequence, which may be inserted in a region distinct from the IL18bp gene sequence.

Foreign Gene Sequence

The foreign gene sequence may be any nucleic acid sequence or molecule not naturally present in a SPV genome, or not naturally present at such a location in a SPV genome.

A foreign gene sequence typically comprises a nucleic acid sequence encoding an mRNA, a peptide or a polypeptide (or protein). The foreign gene sequence may, for instance, encode various types of active molecules, such as an antigen, adjuvant, cytokine, lymphokine, growth factor, enzyme, label, etc.

In a preferred embodiment, the foreign gene sequence encodes an antigen (peptide, polypeptide or protein antigen) from a pathogen of a porcine infectious disease, and most preferably an antigen from a virus, bacterium, fungus, or protozoa. Within the context of the invention, a peptide typically designates a molecule comprising from 4 to 30 amino acids. A polypeptide is any amino acid polymer comprising more than 30 amino acids. The term polypeptide includes full length proteins.

The foreign gene sequence preferably encodes a peptide or polypeptide (e.g., glycoprotein, capsid protein, or fragment thereof) of a virus or pathogen selected from porcine circovirus (PCV1, PCV2, PCV2a, PCV2b, PCV2d, PCV3), *Actinobacillus pleuropneunomia*; Adenovirus; Alphavirus such as Eastern equine encephalomyelitis viruses; *Balantidium coli*; *Bordetella bronchiseptica*; *Brachyspira* spp., preferably *B. hyodyentheriae*, *B. pilosicoli*, *B. innocens*, *Brucella suis*, preferably biovars 1, 2 and 3; Classical swine fever virus, African swine fever virus; *Chlamydia* and *Chlamydophila* sp. and preferably *C. pecorum* and *C. abortus*; *Clostridium* spp., preferably *Cl. difficile*, *Cl. perfringens* types A, B and C, *Cl. novyi*, *Cl. septicum*, *Cl. tetani*; Digestive and respiratory Coronavirus; *Cryptosporidium parvum*; *Eimeria* spp; *Eperythrozoonis suis* currently named *Mycoplasma haemosuis*; *Erysipelothrix rhusiopathiae*; *Escherichia coli*; *Haemophilus parasuis*, preferably subtypes 1, 7 and 14; Hemagglutinating encephalomyelitis virus; Isospora suis; Japanese Encephalitis virus; *Lawsonia intracellulars*; *Leptospira* spp., preferably *Leptospira australis*, *Leptospira canicola*, *Leptospira grippotyphosa*, *Leptospira icterohaemorrhagicae*, *Leptospira interrogans*, *Leptospira pomona* and *Leptospira tarassovi*; *Mannheimia haemolytica*; *Mycobacterium* spp. preferably, *M. avium*, *M. intracellular* and *M. bovis*: *Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp. preferably, *S. thyhimurium* and *S. choleraesuis*; *Staphylococcus* spp. preferably, *S. hyicus*; *Streptococcus* spp., preferably Strep, suis; Swine cytomegalovirus; Swine herpes virus; Swine influenza virus; Swinepox virus; *Toxoplasma gondii*; Vesicular stomatitis virus or virus of exanthema of swine.

In a particularly preferred embodiment, the foreign gene sequence encodes a PCV2 antigen, particularly a PCV2 protein or peptide, even more particularly a PCV2 capsid (e.g., ORF2) protein or peptide.

The foreign gene sequence may contain a transcriptional promoter to allow or increase expression of the encoded mRNA or polypeptide. The promoter used may be a synthetic or natural promoter, including a swinepox promoter, a poxvirus promoter, or a promoter derived from different viruses or cells such as promoters derived from eukaryotic or prokaryotic organisms. Specific examples of promoters include the vaccinia virus 7.5-kD promoter (P7.5k) (Davison A. J. et al., J. Mol. Biol., 210(4):749-69 (1989)), 11-kD promoter (P11k) (Bertholet et al., Proc. Nat. Acad. Sci., 82:2096-2100 (1985)) or 28-kD promoter (P28k) (Weir J. P. & Moss B., J. Virol. 61:75-80 (1987)), or an artificial synthetic Poxvirus promoter (Ps), the thymidine kinase promoter of herpesvirus (Ross L. J., Gen. Virol. 74:371-377 (1993)), gB protein promoter (supra) of HVT or MDV, the IE promoter of human cytomegalovirus (HCMV) (Alting-Mess M. A., Nucleic Acids Res., 17:9494 (1989)), SV40 promoter (Gunning P., Proc. Natl. Acad. Sci., 84:4931-4835 (1987)), [beta] actin promoter (supra, and Kost A. T., Nucleic Acids Res., 11:8287-8301 (1983)), [beta]-globin promoter (Spitzner J. R., Nucleic Acids Res., 18:1-11 (1990)), the LTR promoter of Rous sarcoma virus (Fiek A. et al., Nucleic Acids Res., 20:1785 (1992)), and the like. In addition, promoters of the structural proteins or the essential genes of SPV can also be used.

rSPV of the invention may contain several foreign gene sequences, located in a same cloning region and/or in distinct cloning sites.

In a particular embodiment, the rSPV of the invention comprises at least 2 foreign gene sequences encoding two distinct antigens (from a same or distinct pathogen). In this regard, in a further particular embodiment, the rSPV of the invention comprises at least a foreign gene sequence encoding a PCV2 antigen and a foreign gene sequence encoding a distinct antigen. In another particular embodiment, the rSPV of the invention comprises a foreign gene sequence encoding an antigen and a foreign gene sequence encoding an adjuvant or a cytokine.

In a further particular embodiment, the rSPV of the invention comprises at least two foreign gene sequences each encoding a PCV2 antigen, particularly each gene sequence encodes an ORF2 protein or peptide, which may be the same of different.

In this regard, another embodiment of the invention relates to a recombinant virus comprising at least two foreign gene sequences each encoding a PCV2 ORF2 protein or peptide, wherein each of said foreign gene sequences contain a different cell-addressing signal allowing expression of the PCV2 ORF2 protein or peptide in different compartments of the cell. In particular, in a preferred embodiment, one of said foreign gene sequence encodes a cytoplasmic PCV2 ORF2 protein or peptide and the other encodes a PCV2 ORF2 protein or peptide exposed at the cell surface (outside cell membrane expression). The invention indeed shows that co-expression of a PCV2 ORF2 protein or peptide antigen in two different cell compartments generates a stronger immune response in vivo, allowing better protection of the animal. In a particular embodiment, cell-membrane addressing of an ORF2 protein or peptide is achieved using a cell-membrane addressing peptide derived from B5R gene of Vaccinia virus, as described in WO2014/167060. Alternatively, other cell-addressing sequences may be considered.

In a particular embodiment, the invention relates to a rSPV comprising at least two foreign gene sequences each encoding a PCV2 antigen, particularly an ORF2 protein or peptide, wherein one foreign gene sequence is located in the viral genome in place of deleted viral IL18bp gene sequence, and one foreign gene sequence is located in the viral genome in place of deleted viral TK or ARP gene sequence, and further wherein one of said foreign gene sequences allows cytoplasmic expression of the PCV2 antigen and the other of said foreign gene sequences allows cell membrane exposure of the PCV2 antigen.

In multivalent rSPVs of the invention, the at least two foreign gene sequences may be under the control of the same or distinct promoters, and in the same or opposite orientation.

Nucleic Acid Molecules

The invention also relates to nucleic acid molecules comprising the genome of a rSPV of the invention. Nucleic acid molecules of the invention may be DNA or RNA, double-stranded or single-stranded. Single-stranded DNA or RNA may be the coding strand, also known as the sense strand, or it may be the non-coding strand, also referred to as the anti-sense strand. The invention also relates to variants or analogs of such nucleic acid molecules, e.g., molecules having at least 85%, 90%, 95%, 96%, 97%, 98% or more sequence identity thereof.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 5371 1) (Needleman, S. B. and Wunsch, C D., (1970), Journal of Molecular Biology, 48, 443-453). Using GAP with the following settings for DNA sequence comparison: GAP creation penalty of 5.0 and GAP extension penalty of 0.3. Nucleic acid molecules may be aligned to each other using the Pileup alignment software, available as part of the GCG program package, using, for instance, the default settings of gap creation penalty of 5 and gap width penalty of 0.3.

Suitable experimental conditions for determining whether a given nucleic acid molecule hybridizes to a specified nucleic acid may involve pre-soaking of a filter containing a relevant sample of the nucleic acid to be examined in 5×SSC for 10 minutes, and pre-hybridization of the filter in a solution of 5×SSC, 5×Denhardt's solution, 0.5% SDS and 100 [mu]g/ml of denatured sonicated salmon sperm DNA, followed by hybridization in the same solution containing a concentration of 10 ng/ml of a P-dCTP-labeled probe for 12 hours at approximately 45<0>C, in accordance with the hybridization methods as described in Sambrook et al. (1989; Molecular Cloning, A Laboratory Manual, 2nd edition, Cold Spring Harbour, N.Y.). The filter is then washed twice for 30 minutes in 2×SSC, 0.5% SDS at least 55<0>C (low stringency), at least 60<0>C (medium stringency), at least 65<0>C (medium/high stringency), at least 70<0>C (high stringency), or at least 75<0>C (very high stringency). Hybridization may be detected by exposure of the filter to an x-ray film.

The nucleic acid molecules according to the invention may be provided in the form of a nucleic acid molecule per se such as naked nucleic acid molecules; a vector; virus or host cell etc. Vectors include expression vectors that contain a nucleic acid molecule of the invention.

Host Cells

In a further embodiment of the invention, there is provided a host cell transformed with a nucleic acid or with a rSPV according to the invention. Such cells can produce rSPVs of the invention. Suitable examples of host cells are known to those skilled in the art or can be readily selected by those skilled in the art. Host cells are preferably eukaryotic cells such as mammalian (e.g., pig), fungal (e.g. *Saccharomyces cerevisiae, pichia, aspergillus, fusarium*), insect and plant cells. Specific examples of host cells are swine kidney cells, such as ESK-4 cells (CL-184).

Vaccine Compositions and Methods

The term "vaccine" as used herein includes any composition which may be used to cause, stimulate or amplify an immune response in an animal (e.g., pigs) against a pathogen. Particular examples of vaccines of the invention are composition able to cause or stimulate or amplify immunity against a PCV2 virus. In a vaccine of the invention, the at least one foreign gene sequence shall encode an antigen or an adjuvant.

The term "immunization" includes the process of delivering an immunogen to a subject. Immunization may, for example, enable a continuing high level of antibody and/or cellular response in which T-lymphocytes can kill or suppress the pathogen in the immunized non-human animal, such as pig, which is directed against a pathogen or antigen to which the animal has been previously exposed.

Vaccines of the invention comprise an immunologically effective amount of a rSPV or nucleic acid or cell as described above in a pharmaceutically acceptable vehicle.

In practice, the exact amount required for an immunologically effective dose may vary from subject to subject depending on factors such as the age and general condition of the subject, the nature of the formulation and the mode of administration. Appropriate "effective amount" may be determined by one of ordinary skill in the art using only routine experimentation. For instance, methods are known in the art for determining or titrating suitable dosages of a vaccine to find minimal effective dosages based on the weight of the non-human animal subject, concentration of the vaccine and other typical factors. In a typical embodiment, the vaccine comprises a unitary dose of between 10 and 10,000,000 $TCID_{50}$, preferably between 100 and 1,000,000 $TCID_{50}$, even more preferably of between 1,000 and 100,000 $TCID_{50}$, of a rSPV of the invention. $TCID_{50}$ designates the median tissue culture infective dose, i.e., the amount of virus that produces pathological change in 50% of inoculated cell cultures.

The dosage of the vaccine, concentration of components therein and timing of administering the vaccine, which elicit a suitable immune response, can be determined by methods such as by antibody titrations of sera, e.g., by ELISA and/or seroneutralization assay analysis and/or by vaccination challenge evaluation.

Vaccines may comprise other ingredients, known per se by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, or preservatives, depending on the route of administration.

Examples of pharmaceutically acceptable carriers, excipients or diluents include, but are not limited to demineralised or distilled water; saline solution; vegetable based oils such as peanut oil, arachis oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-[alpha], IFN-[beta], IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

Vaccines may comprise antigens from several pathogens, such as PCV2, *Actinobacillus pleuropneunomia*; Adenovirus; Alphavirus such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; lsospora suis; Japanese Encephalitis virus; Lawsonia intracellulars; *Leptospira* spp., preferably *Leptospira australis, Leptospira canicola, Leptospira grippotyphosa, Leptospira icterohaemorrhagicae, Leptospira interrogans, Leptospira pomona* and *Leptospira tarassovi; Mannheimia haemolytica; Mycobacterium* spp. preferably, *M. avium, M. intracellular* and *M. bovis: Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp. preferably, *S. thyhimurium* and *S. choleraesuis; Staphylococcus* spp. preferably, *S. hyicus; Streptococcus* spp., preferably Strep, suis; Swine cytomegalovirus; Swine herpes virus; Swine influenza virus; Swinepox virus; *Toxoplasma gondii*; Vesicular stomatitis virus and/or virus of exanthema of swine.

The vaccine compositions of the invention may be liquid formulations such as an aqueous solution, water-in-oil or oil-in-water emulsion, syrup, an elixir, a tincture, a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents.

The route of administration can be percutaneous, via mucosal administration, or via a parenteral route (intradermal, intramuscular, subcutaneous, intravenous, or intraperitoneal). The vaccine of the invention can conveniently be administered intranasally, transdermally (i.e., applied on or at the skin surface for systemic absorption), parenterally, ocularly, etc. The parenteral route of administration includes, but is not limited to, intramuscular, intravenous, intraperitoneal routes and the like.

The vaccines of the invention can be administered as single doses or in repeated doses. The vaccines of the invention can be administered alone, or can be administered simultaneously or sequentially administered with one or more further compositions, such as for example other porcine immunogenic or vaccine compositions. Where the compositions are administered at different times the administrations may be separate from one another or overlapping in time.

The present invention also relates to methods of immunizing or inducing an immune response in a non-human mammal (e.g., pigs) comprising administering to said mammal a rSPV or a nucleic acid, or a cell or a vaccine as described above.

Vaccines of the invention are preferably administered to pigs, adult pigs, but also to young pigs, piglets or to pregnant sow. Vaccination of pregnant sows is advantageous as it can confer passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. Desirably, the vaccine is administered to a subject who has not yet been exposed to the pathogen.

The present invention also provides a container comprising an immunologically effective amount a rSPV, nucleic acid, cell or vaccine as described above. The invention also provides vaccination kits comprising an optionally sterile container comprising an immunologically effective amount of the vaccine, means for administering the vaccine to animals, and optionally an instruction manual including information for the administration of the immunologically effective amount the composition for treating and/or preventing infectious disease.

PCV2 Vaccine

The invention is particularly suited for the treatment (preventive curative) of PCV2 infection and associated diseases.

Currently developed PCV2 vaccines, such as Circovac® (Merial), Ingelvac®, CircoFLEX (Boehringer lngelheim Vetmedica), or Suvaxyn®, are either inactivated PCV2 vaccines or Sub-Unit vaccines. PCV2 Sub-Unit vaccines typically use a purified, recombinant PCV2A capsid protein produced by recombinant expression of the ORF2 gene of PCV2A. In this regard, the protein encoded by ORF2 of PCV2 isolates Imp1011 has been reported in EP1741785. A protein encoded by ORF2 of PCV2 isolate PCV2Rm has been reported in WO2010/061000. The protein encoded by ORF2 of PCV2 isolate 412 has been reported in EP1816200. Another protein encoded by an ORF2 of a further PCV2 isolate has been reported in EP1036180 or EP2225367. Improved synthetic ORF2-type proteins have been described in WO2013/030320 and in WO2014/167060.

In a particular embodiment, the present invention relates to a rSPV as defined above wherein the foreign gene sequence encodes a PCV2 antigen, more preferably a PCV2 protein, polypeptide or peptide. In a more preferred embodiment, the present invention relates to a rSPV as defined above wherein the foreign gene sequence encodes a PCV2 ORF2 polypeptide or a fragment thereof. In a particular embodiment, the ORF2 is selected from ORF2 of PCV2 isolates Imp1011, PCV2Rm, or 412, or a ORF2 having at least 80% sequence identity to such proteins, or an immunogenic fragment thereof comprising at least 10, 15, more preferably at least 20 contiguous amino acid residues thereof.

In a further particular embodiment, the invention relates to a rSPV comprising at least two foreign gene sequences each encoding a PCV2 antigen, particularly an ORF2 protein or peptide, wherein one foreign gene sequence is located in the viral genome in place of deleted viral IL18bp gene sequence, and one foreign gene sequence is located in the viral genome in place of deleted viral TK or ARP gene sequence, and further wherein one of said foreign gene sequences allows cytoplasmic expression of the PCV2 antigen and the other of said foreign gene sequences allows cell membrane exposure of the PCV2 antigen.

In one embodiment, the rSPV comprises at least two foreign gene sequences each encoding an ORF2 protein or peptide from different genotypes, preferably from PCV2b and PCV2d.

A further aspect of the invention relates to methods of treating and/or preventing a PCV2 associated disease in a non-human mammal, and to methods of immunizing or vaccinating a non-human animal subject, such as pigs, swine, sow, piglet, against PCV2 infection, comprising administering to said animal subject a rSPV, a nucleic acid, a cell, or vaccine composition as defined above.

PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Preferably, a non-human animal subject, such as pig, is protected to an extent in which one to all of the adverse physiological symptoms or effects of PCV2 infections are significantly reduced, ameliorated or totally prevented.

In one embodiment, the vaccine compositions of the invention are administered to a pig susceptible to or otherwise at risk for PCV2 infection to enhance the subject own immune response capabilities.

Preferably, the subject is a pig which is in need of vaccination against Postweaning Multisystemic Wasting Syndrome (PMWS) and/or Porcine Dermatitis and Nephropathy Syndrome (PDNS).

Further aspects and advantages of the invention shall be disclosed in the following experimental section, which illustrates the claimed invention.

EXAMPLES

Example 1

Construction of Plasmids for Making Recombinant SPV (1) Constructing pSP91 (FIG. 1)
The SPV genomic DNA was prepared as follows:
SPV kasza strain (VR-363) and embryonic swine kidney cell, ESK-4 cells (CL-184) could be purchased from the American Type Culture Collection (ATCC). The ESK-4 cells were routinely cultured at 37.0 in 5% CO2 in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028). For SPV genomic DNA preparation, confluent ESK-4 cells in a 225 cm2 flask were infected with SPV and incubated for 6 days until the cells were showing 100% cytopathic effect (CPE). The infected cells were then harvested by scraping the cells into the medium and centrifuging at 1300 rpm for 5 min. The medium was decanted, and the cell pellet was gently resuspended in 2 ml Phosphate Buffer Saline (PBS: 1.5 g Na2HPO4, 0.2 g KH2PO4, 0.8 g NaCl and 0.2 g KCl per litter H2O) and subjected to two successive freeze-thaws. Cellular debris was then removed by centrifuging at 3000 rpm for 5 min at 4° C. SPV virions, present in supernatant, were then pelleted by centrifugation at 20,000×g for 20 min at 4° C. The resultant pellet was then suspended with 10 mM Tris pH7.5. SPV genomic DNAs were then extracted from the SPV virions by suspending with the lysis buffer (20 mM Tris, pH9, 0.1M NaCl2, 5 mM EDTA, 0.1% SDS, 0.2 mg/ml proteinase K) and incubating at 60.0 for 5 min. Phenol:chlororoform (1:1) extraction was conducted two times, and the sample precipitated by the addition of two volumes of ethanol and centrifugation. The supernatant was decanted, and the pelett (SPV DNA) was air dried and rehydrated in 10 mM Tris pH7.5, 1 mM EDTA at 4° C.

The flanking regions of interleukin 18 binding protein (IL-18bp) gene in the SPV genome were cloned by Polymerase Chain Reaction (PCR). Two primers (synthetic oligonucleotides), SP6030F and SP9574R shown in SEQ ID NOs: 1 and 2 were purchased from Takara Bio. PCR reaction was conducted using LA Taq polymerase (Takara Bio) and a primer set of SP6030F and SP9574R with SPV DNA as a template according to the producer's protocol.

```
SEQ ID NO: 1:
CGAATTCATTCCTTTATCTTTA

SEQ ID NO: 2:
GGAACTACGTTATACGATCAT
```

The amplified DNA of about 3.5 kbp was confirmed by a 0.8% agarose gel electrophoresis, and purified from the gel using the QIAquick Gel Extraction Kit (Qiagen). The purified DNA fragment was cloned into pCR4-TOPO vector (Invitrogen) according to the producer's protocol. 12 white ampicillin-resistant transformants were picked up and grown in LB broth containing 50 micro-g/ml ampicillin, and each plasmid was prepared with QuickLyse Miniprep Kit (Qiagen). Each plasmid was digested with ScaI, and two kinds of candidate plasmids (both directions of inserted DNA) were selected. The inserted DNAs of them were sequenced with Dye Terminator Cycle Sequencing reagent (DTCS) and CEQ2000XL sequencer (Beckman Coulter). One of the candidate plasmids, pCR-SPV6030/9574 (#1), was confirmed that it contained the DNA fragment from 6,030 nt to 9,574 nt of SPV genomic DNA (GeneBank Acc: NC 003389) and used as a basic plasmid (FIG. 1).

Next, PCR mutagenesis was conducted to delete a part of the IL-18bp gene (nt31-382) and to introduce the multiple restriction enzyme sites using pCR-SPV6030/9574 (#1) as a template and using two kinds of primer sets, (1) SEQ ID NOs: 3 and 4 or (2) SEQ ID NOs: 5 and 6.

```
SEQ ID NO: 3:
TTCGCCCTTACGGTACCATTCCTTTATCTTTATAAACG
```

SEQ ID NO: 4:
CTATAATATTAAATAAGCTTTATGGAGTTGTTTAAATAC

SEQ ID NO: 5:
CACACGATAACACTGCAGTCCACATATTACGGTTC

SEQ ID NO: 6:
GCCGCGAATTCGCCCTCGAGGAGCTCACTACG

Each PCR products were applied to a 0.8% agarose gel electrophoresis and purified using the QIAquick Gel Extraction Kit. The purified DNA fragment, which was amplified by PCR using a primer set of SEQ ID NOs: 3 and 4, was digested with two restriction enzymes, KpnI and HindIII, and ligated with the same restriction enzymes-cut-pBluescript KS(+) (Stratagene). The resulted plasmid pBS-9L (Kpn . . . Hin) (FIG. 1) was digested with SacI and PstI, and the same restriction enzymes-cut DNA fragment amplified by PCR using a primer set of SEQ ID NOs: 5 and 6, was inserted into it. The resulting plasmid was named as pSP90 (FIG. 1).

Between EcoRI and HindIII sites in the multi-restriction enzyme sites of pSP90 were replaced with the oligonucleotide adapter prepared by annealing two synthetic DNA oligonucleotides of SEQ ID NOs: 7 and 8. The resulting plasmid was named as pSP91 (FIG. 1).

SEQ ID NO: 7:
AATTGCCCGGGTACCGTCGATCGACTTTTTATGGCCCCCCCGGCCA

SEQ ID NO: 8:
AGCTTGGCCGGGGGGGCCATAAAAAGTCGATCGACGGTACCCGGGC (2) Constructing pSP911-ORF2cc and pSP911-Ess_ORF2cc (FIG. 2)

The sequence between KpnI and PstI of pSP91 were replaced with the synthetic adapter shown in SEQ ID NO: 9 to insert the vaccinia virus 11-kD promoter, which was reported as strong late promoter (A. J. Davison and B. Moss. J. Mol. Biol. 210, 771-784, 1989) into it. The resulted plasmid was designated as pSP911 (FIG. 2).

SEQ ID NO: 9:
GGTACCGAGCTCGGTAGCCCGGGCCATGGTAGATCCTCTAGAGGATCCAA
TTCATTTATAGCATAGAAAAAAACAAAATGAAATTCTACTATATTTTCTG
CAG

Foreign gene sequences encoding ORF2 of PCV2 were synthesized: A first sequence containing a codon-changed ORF2 of PCV2 was prepared (designated as ORF2cc). This sequence allows cytoplasmic expression. Another sequence was prepared containing the same codon-changed ORF2 of PCV2, but modified to further include a cell-membrane addressing sequence (designated as Ess_ORF2cc). This sequence allows cell-membrane exposure of the encoded polypeptide. The sequences of synthesized ORF2cc and Ess_ORF2cc were SEQ ID NO:10 and 11, respectively.

SEQ ID NO: 10:
ATGACCTACCCTAGAAGAAGATATAGGAGGCGGAGGCATCGGCCACGGAG

TCACCTGGGACAAATTCTGCGGAGAAGGCCATGGTTGGTGCATCCAAGAC

ATAGATATAGGTGGAGGAGAAAGAACGGAATCTTTAATACAAGACTGTCT

AGAACTTTTGGGTACACCGTGAAAAGAACAACCGTGAGGACCCCATCTTG

GGCCGTTGATATGATGAGGTTTAACATCAACGATTTCTTCCCTCCTGGGG

GAGGATCTAATCCTAGATCCGTTCCATTCGAGTATTATAGGATCAGGAAA

GTGAAAGTGGAGTTTTGGCCATGTAGCCCAATTACTCAAGGAGATAGAGG

TGTTGGATCTAGCGCCGTGATCCTGGACGACAATTTCGTGACCAAAGCAA

CCGCACTGACTTACGATCCTTACGTGAATTATTCTAGCAGACACACTATT

ACTCAACCATTTAGCTATCACAGCAGATATTTCACTCCTAAGCCAGTGCT

GGACAGCACCATCGACTATTTTCAGCCTAATAATAAGAGGAATCAACTTT

GGCTTAGGCTTCAGACCGCCGGGAACGTGGATCACGTGGGATTGGGAACC

GCATTTGAGAATTCTATTTATGATCAAGAGTATAACATTAGAGTGACTAT

GTACGTGCAGTTTAGGGAGTTCAACCTGAAAGATCCACCTCTGAATCCAT

AA

SEQ ID: NO: 11:
ATGAAAACGATTTCCGTTGTTACGTTGTTATGCGTACTACCTGCTGTTGT

TTATTCAACATGTACTGTACCCACTATGAATAACGCTAAATTGACGTCTA

CCGAAACATCGTGGAAAAAAGAGAAAGGAGTCTTGAACACCAGATTGTCT

AGAACCTTCGGTTACACCATTAAGAGAACCACCGTCAAAACCCCATCTTG

GGCTGTCGATATGATGAGATTCAACATCAACGATTTCGTCCCACCTGGTG

GTGGATCAAACCCTAGATCCGTTCCATTCGAGTACTACAGAATCAGAAAA

GTCAAAGTCGAGTTCTGGCCATGCTCTCCTATTACTCAGGGTGATAGAGG

AGTTGGATCAACTGCCGTCATCTTGGATGACAACTTCGTCACTAAGGCTA

CTGCCTTGACCTACGATCCTTACGTCAATTACTCTAGTAGACACACCATC

ACCCAACCATTCTCATACCATTCCAGATACTTCACTCCAAAACCTGTCTT

GGACTCAACCATCGATTACTTTCAACCAAACAACAAGAGAAACCAATTGT

GGTTGAGATTGCAAACTGCCGGTAACGTCGATCATGTCGGATTGGGAACC

GCCTTCGAAAACTCCAAATACGACCAGGAGTACAACATTAGAGTCACCAT

GTACGTCCAATTCAGAGAGTTCAACTTGAAGGACCCACCATTGAACCCAT

AA

These synthetic genes—ORF2cc and Ess_ORF2cc—conjugated BamHI or SalI site at 5' or 3'terminus were digested with BamHI and SalI, and inserted into the pSP911 cut with BamHI and SalI. The resulted plasmids were designated as pSP911-ORF2cc or pSP911-Ess_ORF2cc (FIG. 2), and used for making each of recombinant swinepox virus—SVR15 or SVR14—respectively.

(3) Constructing pSP53-ORF2 (FIG. 3)

The Ankirin Repeat Protein (ARP) gene of SPV was obtained from plasmid pNZSP52L (JP2003-111591A). The synthetic adapter shown in SEQ ID NO: 12 was replaced into the region between HindIII and EcoRI of the pNZSP52L, and the resulted plasmid was designated as pSP53.

The PCV2-ORF2 gene used is shown in SEQ ID NO: 13. The gene was synthesized, digested with BamHI and SalI, and inserted into BamHI and SalI sites of pSP53. The resulted plasmid was designated as pSP53-ORF2 (FIG. 3), and used for making two recombinant swinepox viruses, SVR16 and SVR17.

SEQ ID NO: 12:
AAGCTTGGCCGGGGGGGCCAGCTCGGTACATAAAAATGTCGACGGATCCG

AGTGCAATAAATTAGAATAGTTTTTCAATTTTTACGCGTAATTAATTATT

GTATTTATTATTTATATGCCAAAAAAAAAAAAAAAAAAAAGCTTCATAAA

AAGTCGATCGACGGTACCACCCGGGGATCGATCCAAAAAAATCTTTCGGC

CTGCATGAATGGCCTTGTTGATCGCTTATTATTATTTTTGACACCAGACC

AACTGGTAATGGTAGCGACCGGCGCTCAGCTGGAATTC

SEQ ID NO: 13:
GGATCCATGACGTATCCAAGGAGGCGTTACCGCAGAAGAAGACACCGCCC

CCGCAGCCATCTTGGCCAGATCCTCCGCCGCCGCCCCTGGCTCGTCCACC

CCCGCCACCGCTACCGTTGGAGAAGGAAAAATGGCATCTTCAACACCCGC

CTCTCCCGCACCTTCGGATATACTGTCAAGCGTACCACGGTCACAACGCC

CTCCTGGGCGGTGGACATGATGAGATTTAAACTTGACGACTTTGTTCCCC

CGGGAGGGGGACCAACAAAATCTCTATACCCTTTGAATACTACAGAATA

AGAAAGGTTAAGGTTGAATTCTGGCCCTGCTCCCCCATCACCCAGGGTGA

TAGGGGAGTGGGCTCCACTGCTGTTATTCTAGATGATAACTTTGTACCAA

AGGCACCAGCCCTAACCTATGACCCATATGTAAACTACTCCTCCCGCCAT

ACAATCCCCCAACCCTTCTCCTACCACTCCCGTTACTTCACACCCAAACC

TGTTCTTGACTCCACTATTGATTACTTCCAACCAAATAACAAAAGGAATC

AGCTTTGGCTGAGGCTACAAACCTCTAGAAATGTGGACCACGTAGGCCTC

GGCACTGCGTTCGAAAACAGTAAATACGACCAAGACTACAATATCCGTGT

AACCATGTATGTACAATTCAGAGAATTTAATCTTAAAGACCCCCCACTTA

ACCCCTAAGTCGAC (4) Construction of pSP72-ORF2 (FIG. 4)

The flanking region of thymidine kinase (TK) gene in the SPV genome were cloned by Polymerase Chain Reaction (PCR). Two primers (synthetic oligonucleotides), SP54242F and SP57617R shown in SEQ ID NOs: 14 and 15 were purchased from Takara Bio. PCR reaction was conducted using LA Taq polymerase (Takara Bio) and a primer set of SP54242F and SP57617R with SPV DNA as a template according to the producer's protocol.

SEQ ID NO: 14:
AATATTACGGGTGCTGTTT

SEQ OD NO: 15:
AAAAACATCGTATTCCTG

The amplified DNA of about 3.4 kbp was confirmed by a 0.8% agarose gel electrophoresis, and purified from the gel using the QIAquick Gel Extraction Kit (Qiagen). The purified DNA fragment was cloned into pCR4-TOPO vector (Invitrogen) according to the producer's protocol. 14 white ampicillin-resistant transformants were picked up and grown in LB broth and each plasmid was prepared with QuickLyse Miniprep Kit (Qiagen). Each plasmid was digested with SpeI, and two kinds of candidate plasmids (both directions of inserted DNA) were selected. The inserted DNAs of them were sequenced with Dye Terminator Cycle Sequencing reagent (DTCS) and CEQ2000XL sequencer (Beckman Coulter). One of the candidate plasmids, pCR-SPV54242/57617 (#2), was confirmed that it contained the DNA fragment from 54,242 nt to 57,617 nt of SPV genomic DNA (GeneBank Acc: NC 003389) and used as a basic plasmid (FIG. 4).

Next, PCR mutagenesis was conducted to delete a part of the TK gene (nt59-536) and to introduce the multiple restriction enzyme sites using pCR-SPV54242/57617 (#2) as a template and using two kinds of primer sets, (1) SEQ ID NOs: 16 and 17 or (2) SEQ ID NOs: 18 and 19.

SEQ ID NO: 16:
CGTTCATGTTAAGCTTAACCTGAAATATTG

SEQ ID NO: 17:
GTTTAAACGAATTCGGTACCCTTAAAAACATCG

SEQ ID NO: 18:
CGCCGAGCTCGAGAATATTACGGGTGCTGTTTTTAC

SEQ ID NO: 19:
CCAGACTGCAGAGAACATAGGTCCTAATATAAG

Each PCR products were applied to a 0.8% agarose gel electrophoresis and purified using the QIAquick Gel Extraction Kit. The purified DNA fragment, which was amplified by PCR using a primer set of SEQ ID NOs: 16 and 17, was digested with two restriction enzymes, KpnI and HindIII, and ligated with the same restriction enzymes-cut-pBluescript KS(+) (Stratagene). The resulted plasmid pBS-TKR (Kpn . . . Hin) (FIG. 4) was digested with SacI and PstI, and the same restriction enzymes-cut DNA fragment amplified by PCR using a primer set of SEQ ID NOs: 18 and 19, was inserted into it. The resulted plasmid was named as pSP70 (FIG. 4).

The synthetic adapter shown in SEQ ID NO: 12 was replaced into the region between HindIII and EcoRI of the pSP70, and the resulted plasmid was designated as pSP711. The DNA fragment of 'P7.5 promoter—LacZ' gene cassette derived from pNZ76, which was cut with HindIII and SmaI of pNZ76 and followed by blunting by DNA polymerase (described in the U.S. Pat. No. 5,387,519) was ligated into SmaI site of pSP711. The resulting plasmid was named as pSP721 (FIG. 4), and 'P7.5-LacZ' gene cassette was inserted into TK gene. The synthetic PCV2-ORF2 gene shown in SEQ ID NO: 13 was digested again with BamHI and SalI, and inserted into BamHI and SalI sites of pSP721, and the resulting plasmid was named as pSP72-ORF2 (FIG. 4). This plasmid was used as a homology plasmid to make a recombinant SPV, SVR20.

Example 2

Producing Recombinant Swinepox Viruses (rSPVs)

(1) Producing rSPVs, SVR14 and SVR15 (FIG. 5)

Recombinant SPVs were generated in ESK-4 cells by homologous recombination between wild-type SPV genome and homology plasmid vectors. Sub-confluent ESK-4 cells in a 6-well plate were infected with wild-type SPV (wtSPV), and 17 hr later the wtSPV-infected cells were transfected with 2 µg of pSP911-Ess_ORF2cc or pSP911-ORF2cc using Lipofectamin Plus reagent (Invitrogen) and allowed to incubate at 37.0 for 5 days until cytopathic effect (CPE) had occurred. Cell lysates from infected-transfected cells were transfection seed (TFS) for SVR14 and TFS for SVR15, respectively. They were diluted into 1:20 with Ham's F-12K medium without FBS, and infected into ESK-4 cells in 96-well plates. Seven days later, each supernatant in 96-well plates were transferred to new blank 96-well plates, and infected cells were lysed with lysis buffer (20 mM Tris-Cl, 0.1M NaCl, 5 mM EDTA, 0.1% SDS, 200 µg/ml protenase K) followed by heat treatment (60° C. 5 min, and 98° C. 2 min). These infected-cell-lysed DNA samples were screened by qPCR using SYBR-Green reagent (Bio-Rad Catalog #: 170-8882) with a primer set of SEQ ID NO: 20 and SEQ ID NO: 21.

SEQ ID NO: 20
AAGTGGAGTTTTGGCCATGT

SEQ ID NO: 21
TCCAGCACTGGCTTAGGAGT

Samples showing DNA-amplifying signal by qPCR were positive, and the corresponded supernatants were forwarded to the next step of screening. Screening was repeated until all appeared plaques were stained with immunofluorescence assay (IFA) using anti-PCV2 pig serum (PAB-PCV2, VMR) as the $1^{st}$ antibody and FITC-conjugated anti-pig IgG (F1638-2ML, SIGMA) as the $2^{nd}$ antibody.

Two wtSPV-free recombinant viruses (G2C2C4 and D10E5F5 clones) were purified from TFS for SVR14 and for SVR15 through three rounds of screening, and designated as SVR14 and SVR15, respectively.

(2) Producing rSPVs, SVR16 and SVR17 (FIG. 5)

Recombinant SPV, SVR16 was generated by homologous recombination between recombinant SPV, SVR15 genome and the homology plasmid vector, pSP53-ORF2. And SVR17 was generated by homologous recombination between SVR 14 genome and the homology vector, pSP53-ORF2. Sub-confluent ESK-4 cells in a 6-well plate were infected with SVR15 or SVR 14, and 17 hr later the rSPV-infected cells were transfected with 2 µg of pSP53-ORF2 using lipofectamine Plus reagent. After CPE appeared, cell lysates (TFS for SVR16 and for SVR17) from infected and transfected cells were screened for recombinant plaques expressing β-galactosidase by the addition of 0.5 mg/ml Bluo-gal (Invitrogen Cat. No.: 15519-028) in the nutrient agarose overlay. The purified recombinant viruses were gotten through 3-4 rounds of screening until all plaques were β-galactosidase positive, and designated as SVR16 and SVR17, respectively.

(3) Producing rSPV, SVR20 (FIG. 5)

Recombinant SPV, SVR20 was generated by homologous recombination between recombinant SPV, SVR14 genome and the homology plasmid vector, pSP72-ORF2. Sub-confluent ESK-4 cells in a 6-well plate were infected with SVR 14, and 17 hr later the SVR14-infected cells were transfected with 2 µg of pSP72-ORF2 using lipofectamine Plus reagent. After CPE appeared, cell lysates (TFS for SVR20) from infected and transfected cells were screened for recombinant plaques expressing β-galactosidase by the addition of 0.5 mg/ml Bluo-gal (Invitrogen Cat. No.: 15519-028) in the nutrient agarose overlay. The purified recombinant viruses were gotten through 3-4 rounds of screening until all plaques were β-galactosidase positive, and designated as SVR20.

Example 3

In Vitro Analysis of Recombinant SPVs (1) Confirming Genome Structures and Stability Post Passages of SVR14 and SVR15 by PCR To confirm genome structures of purified SVR14 and SVR15, their genomic DNAs were prepared as well as the procedures described in Example 1 (1), and used as no passage (+0p) templates for PCR. And to confirm genome stability of SVR14 and SVR15, they were passed to ESK-4 cells 15 times (+15p), and prepared as well as +0p. These genome DNAs were checked by PCR using a primer set of SP7450F and SP8552R shown in SEQ ID NOs: 22 and 23 (FIG. 6).

SEQ ID NO: 22
CAATTGAAACATCTATATATCCTT

SEQ ID NO: 23
CAATGTGAAGCGATAAAATACAG

The results of PCR (FIG. 6) showed that purified SVR14 and SVR15 had expected genome structure and were wild-type SPV free, and that they were stable after 15 times in vitro passages.

(2) Confirming PCV2-ORF2 Protein Expressed by SVR14 and SVR15

Molecular sizes of PCV2-ORF2 proteins expressed by SVR14 and SVR15 were analyzed by a 15% SDS-PAGE and Western blot analysis using anti-PCV2 rat sera. ESK-4 cells were infected with SVR14, SVR15 or wild-type SPV. Six days later, cell lysates were fractionated on a 15% SDS-PAGE. Proteins were transferred onto a polyvinylidene difluoride (PVDF) membrane, Immobilon-P (Merk Millipore, Cat. No.: IPVH08130), and blocked with 0.5% dried milk in PBS. PDVF membrane blots were probed with rat anti-PCV2 sera (1:1,000) as the $1^{st}$ antibody, followed by reacting with biotin conjugated goat anti-rat IgG secondary (1:1,000), and VECTASTAIN ABC-AP Standard Kit (Vector Labs, AK-5000). Membrane blots were developed with alkaline phosphatase substrate, Nitroblue Tetrazolium (NBT)/5-Bromo-4-Chloro-3-Indolyl Phosphate (BCIP).

Results of western blotting showed that SVR14 expressed two kinds of ORF2, molecular sizes of 27 kDa and 25 kDa (FIG. 7). The former 27 kDa protein was presumed to be precursor form, and the latter was presumed to be processed form after cleavage at the end of the signal peptide. On the other hand, SVR15 expressed only 27 kDa protein which were localized in infected cell nuclei (FIG. 7).

(3) Confirming Genome Structures of Double Recombinants SVR16 and SVR17

To confirm genome structures of purified SVR16 and SVR17, their genomic DNAs were prepared as well as the procedures described in Example 1 (1), and used as no passage (+0p) templates for PCR. And to confirm genome stability of SVR16 and SVR17, they were passed to ESK-4 cells 15 times (+15p), and prepared as well as +0p. These genome DNAs were checked by PCR using a primer set of P05-8 and P05-9 shown in SEQ ID NOs: 24 and 25 (FIG. 8).

SEQ ID NO: 24
TATGTCTAAAGGTGCGTCTA

SEQ ID NO: 25
AGTGGCTATATTATCATCCTG

The results of PCR (FIG. 8) showed that purified SVR16 and SVR17 had expected genome structure, and that they were stable after 15 times in vitro passages.

(4) Confirming Genome Structures of Double Recombinant SVR20

To confirm genome structures of purified SVR20, its genomic DNA was prepared according to the procedures described in Example 1 (1), and used as no passage (+0p) templates for PCR. To confirm genome stability of SVR20, it was passed to ESK-4 cells 15 times (+15p), and prepared as for +0p. These genome DNAs were checked by PCR using primer sets of (a) SP7450F and SP8552R shown in SEQ ID Nos: 22 and 23 for IL18bp site, and (b) SP55500F and SP56363R shown in SEQ ID Nos: 26 and 27 for TK site (FIG. 9).

SEQ ID NO: 26
ATACGATTAAGCGATAGTGATA

SEQ ID NO: 27
ATATTATTTTCATTTGTTTCCTA

The results of PCR (FIG. 9) showed that purified SVR20 had expected genome structure, and that it was stable after 15 times in vitro passages.

(5) Confirming PCV2-ORF2 Protein Expressed by SVR16, SVR17 and SVR20

PCV2-ORF2 proteins expressed by recombinant SPVs were analyzed by western blotting. ESK-4 cells in 6-well plates were infected with wild-type SPV, SVR14, SVR15, SVR16, SVR17, or SVR20 at multiplicity of infection (M.O.I.) of 0.1. Six days later, cell lysates were applied to 15% SDS-PAGE and blotted onto a PVDF membrane. After blocking with 0.5% dried milk in PBS, PDVF membrane blots were probed with rat anti-PCV2 sera (1:500) as the $1^{st}$ antibody, followed by reacting with biotin conjugated goat anti-rat IgG secondary (1:1,000), and VECTASTAIN ABC-AP Standard Kit (Vector Labs, AK-5000). Membrane blots were developed with alkaline phosphatase substrate, Nitroblue Tetrazolium (NBT)/5-Bromo-4-Chloro-3-Indolyl Phosphate (BCIP).

Results of western blotting (FIG. 10) surprisingly showed that doubly defective viruses of the invention express the foreign gene more efficiently than mono-defective viruses: SVR16 expressed 25 kDa protein more than SVR15, and SVR17 and SVR20 expressed two kinds of ORF2 (27 kDa precursor and 25 kDa processed protein) more than SVR14.

Example 4

Pig Trial for Safety Test of rSPVs (1) Immunization of Pigs

12 SPF pigs (ZEN-NOH premium pigs) were purchased from National Federation of Agricultural Co-operative Associations (Chiba, Japan) and divided into 4 groups (N=3 per group). Each pig of group 1 to 4 was immunized into the right side of neck using 23G 1.5 inch needle with 1 ml of $10^4$ $TCID_{50}$/ml of SVR16, SVR17, SVR20, or wild-type SPV (wtSPV), respectively at 4-weeks of age.

(2) Observation of Immunized Pigs

The vaccination sites were observed from the 1 day post vaccination (1-DPV) to 18-DPV. During the trial, all pig were healthy and showing no clinical case such as diarrhea or respiratory symptoms except skin reactions at the injection site vaccinated with SVR16, SVR17 or wtSPV. Sizes of redness by the skin inflammatory reaction were quantitatively determined as the cubic content [Width (mm)×Depth (mm)=mm2]. The Width (W) is the X-axis as longer axis direction of redness. The Depth (D) is the Y-axis as shorter axis direction of redness. The redness sizes of immunized pigs were summarized in Table 1 and plotted in FIG. 11.

TABLE 1

Redness sizes ($mm^2$) in pigs of group 1 to 4.

| Group (Vaccine) | Pig Tag | Redness size ($mm^2$) at Day post vaccination (DPV) 1DPV | 2DPV | 3DPV | 4DPV | 5DPV | 6DPV | 7DPV | 8DPV | 9DPV |
|---|---|---|---|---|---|---|---|---|---|---|
| Group 1 | No. 4 | 0 | 0 | 0 | 0 | 0 | 0 | 0 | 0 | 0 |
| (SVR16) | No. 5 | 0 | 0 | 0 | 0 | 0 | 0 | 9.1 | 15.5 | 0 |
| | No. 6 | 0 | 0 | 0 | 0 | 0 | 0 | 7.0 | 23.1 | 0 |
| Group 2 | No. 7 | 0 | 0 | 0 | 0 | 0 | 0 | 33.2 | 38.3 | 23.7 |
| (SVR17) | No. 8 | 0 | 0 | 0 | 0 | 0 | 0 | 10.3 | 26.0 | 14.7 |
| | No. 9 | 0 | 0 | 0 | 0 | 0 | 0 | 16.5 | 24.7 | 12.8 |
| Group 3 | No. 10 | 0 | 0 | 0 | 0 | 0 | 0 | 0 | 0 | 0 |
| (SVR20) | No. 11 | 0 | 0 | 0 | 0 | 0 | 0 | 0 | 0 | 0 |
| | No. 12 | 0 | 0 | 0 | 0 | 0 | 0 | 0 | 0 | 0 |
| Group 4 | No. 13 | 0 | 0 | 0 | 0 | 0 | 0 | 17.5 | 23.3 | 18.7 |
| (wtSPV) | No. 14 | 0 | 0 | 0 | 0 | 0 | 0 | 28.7 | 40.4 | 35.7 |
| | No. 15 | 0 | 0 | 0 | 0 | 0 | 0 | 26.0 | 79.0 | 32.2 |

| Group (Vaccine) | Pig Tag | Redness size ($mm^2$) at Day post vaccination (DPV) 10DPV | 11DPV | 12DPV | 13DPV | 14DPV | 15DPV | 16DPV | 17DPV | 18DPV |
|---|---|---|---|---|---|---|---|---|---|---|
| Group 1 | No. 4 | 0 | 0 | 0 | 0 | 0 | 0 | 0 | 0 | 0 |
| (SVR16) | No. 5 | 0 | 0 | 0 | 0 | 0 | 0 | 0 | 0 | 0 |
| | No. 6 | 0 | 0 | 0 | 0 | 0 | 0 | 0 | 0 | 0 |
| Group 2 | No. 7 | 8.2 | 6.7 | 4.1 | 7.8 | 9.8 | 0 | 0 | 0 | 0 |
| (SVR17) | No. 8 | 6.3 | 4.4 | 2.4 | 3.3 | 4.5 | 0 | 0 | 0 | 0 |
| | No. 9 | 9.6 | 5.7 | 4.2 | 5.6 | 5.7 | 0 | 0 | 0 | 0 |
| Group 3 | No. 10 | 0 | 0 | 0 | 0 | 0 | 0 | 0 | 0 | 0 |
| (SVR20) | No. 11 | 0 | 0 | 0 | 0 | 0 | 0 | 0 | 0 | 0 |
| | No. 12 | 0 | 0 | 0 | 0 | 0 | 0 | 0 | 0 | 0 |
| Group 4 | No. 13 | 11.6 | 10.1 | 7.4 | 14.6 | 17.5 | 12.7 | 8.7 | 7.4 | 5.4 |
| (wtSPV) | No. 14 | 15.7 | 13.7 | 10.4 | 8.5 | 9.1 | 10.5 | 1.3 | 1.8 | 2.0 |
| | No. 15 | 21.5 | 17.3 | 13.8 | 15.2 | 18.0 | 13.6 | 9.9 | 4.7 | 4.3 |

The reddening areas were the largest in pigs vaccinated with wild-type SPV. No reddening was observed at the injection site of pigs immunized with SVR20. These results show that the IL18-bp and TK genes doubly-deleted recombinants are much safer than wild-type SPV. SVR20 appeared particularly attenuated.

Example 5

Second Pig Trial for Immunogenicity and Safety Test of rSPVs (1) Immunization 30 SPF pigs (ZEN-NOH premium pigs) were purchased from National Federation of Agricultural Co-operative Associations (Chiba, Japan) and divided into 6 groups (N=5 per group).

Pigs of group 3 were immunized into the right side of the neck intramuscularly with 1 ml of $10^5$ TCID$_{50}$/ml of SVR20 at 4-weeks of age. Pigs of group 4 were immunized into the right side of the neck intramuscularly with 1 ml of the commercial vaccine for PCV2, Ingelvac CircoFLEX (Boehringer Ingelheim Vetmedica). Pigs of groups 5 and 6 were non-immunized. All pigs vaccinated with SVR20 looked healthy.

(2) PCV2 Challenge to Pigs

After 3 weeks post vaccination, pigs of groups 1 to 5 were challenged by spraying $6\times10^5$ TCID$_{50}$ of PCV2b Rm40 strain (imported from Ceva-Phylaxia, Hungary) into the right nostril. Pigs of group 6 were non-immune and non-challenged control.

(3) PCV2 Load in Lymph Organs

After three weeks post challenge (10 weeks of age), all pigs were euthanized and anatomized. Sections of four lymph nodes, inguinal lymph nodes (ILN), hilar lymph nodes (HLN), tonsils and mesenteric lymph nodes (MLN), were removed using clean, separate scissors and forceps. Sections of them were put into sterile 50 ml Eppendorf tubes and kept at −80° C. until further processing.

The DNAs from organ samples were extracted by the QIAamp DNA Mini Kit (QIAGEN) according to the manufacturer's instructions. PCV2 DNAs were quantified using a TaqMan-based real-time PCR described in J. Virol. Methods, 2004 Dec. 15; 122 (2): 171-178 (PMID: 15542141).

The ratios of PCV2-positive ($>1\times10^3$ copies/mg-organ) pigs are summarized in Table 2.

TABLE 2

PCV2 positive pigs in 4 lymph organs after 3 weeks post challenge.

| # | Group Vac/Challenge | No of PCV2 positive/Total (%) | | | |
|---|---|---|---|---|---|
| | | HLN | ILN | Tonsil | MLN |
| G3 | SVR20/Ch | 1/5 (20) | 0/5 (0) | 1/5 (20) | 0/5 (0) |
| G4 | CircoFlex/Ch | 4/5 (80) | 1/5 (20) | 3/5 (60) | 1/5 (20) |
| G5 | NI/Ch | 5/5 (100) | 5/5 (100) | 5/5 (100) | 4/5 (80) |
| G6 | NI/N-Ch | 0/5 (0) | 0/5 (0) | 0/5 (0) | 0/5 (0) |

Vaccination with doubly-defective viruses of the invention was very effective to inhibit PCV2 load in lymph nodes. In particular, regarding PCV2 load in HLN, all pigs of G5 (non-vaccinated) were PCV2 positive (100%), while only one pig of G3 (SVR20-vaccinated) was positive (20%). Strikingly, the viral load in pigs of G4, vaccinated with commercial anti-PCV2 vaccine, was much higher (80% positive pigs). Regarding PCV2 load in ILN, all pigs of G5 (non-vaccinated) were PCV2 positive (100%), while all pig of G3 (SVR20-vaccinated) were negative (0%). Strikingly, the viral load in pigs of G4, vaccinated with commercial anti-PCV2 vaccine, was higher (20% positive pigs). Regarding PCV2 load in tonsils, all pigs of G5 (non-vaccinated) were PCV2 positive (100%), while only one pig of G3 (SVR20-vaccinated) was positive (20%). Again, the viral load in pigs of G4, vaccinated with commercial anti-PCV2 vaccine, was much higher (60% positive pigs). Regarding PCV2 load in MLN, most pigs of G5 (non-vaccinated) were PCV2 positive (80%), while all pigs of G3 (SVR20-vaccinated) were negative (0%). The viral load in pigs of G4, vaccinated with commercial anti-PCV2 vaccine, was higher (20% positive pigs).

These results show that vaccination with SVR20 gave much stronger protection than with commercial vaccine.

---

The invention claimed is:

1. A recombinant swinepox virus (rSPV) having at least a first and a second defective viral genes, wherein the first defective viral gene is IL18bp gene and the second defective viral gene is the Thymidine Kinase (TK) or Ankirin Repeat Protein (ARP) gene, wherein the viral genes are defective by deletion.

2. The rSPV of claim 1, wherein said rSPV comprises a deletion of at least 50 bp in the TK gene sequence and a deletion of at least 50 bp in the IL18bp gene sequence.

3. The rSPV of claim 1, which comprises a deletion of at least 100 bp in the TK gene sequence and a deletion of at least 100 bp in the IL18bp gene sequence.

4. The rSPV of claim 1, wherein said rSPV comprises a deletion of at least 50 bp in the ARP gene sequence and a deletion of at least 50 bp in the IL18bp gene sequence.

5. The rSPV of claim 1, which further comprises a first foreign gene sequence, located in place of the defective viral TK, ARP or IL18bp gene sequence.

6. The rSPV of claim 2, wherein the rSPV genome comprises a deletion of at least 100 bp in the TK gene sequence and wherein the first foreign gene sequence is located in said deletion.

7. The rSPV of claim 3, wherein said rSPV comprises a first foreign gene sequence located in place of the deleted viral TK gene sequence, and a second foreign gene sequence located in place of the deleted viral IL18bp gene sequence.

8. The rSPV of claim 4, wherein said rSPV comprises a first foreign gene sequence located in place of the deleted viral ARP gene sequence, and a second foreign gene sequence located in place of the deleted viral IL18bp gene sequence.

9. The rSPV of claim 7, wherein the first and/or second foreign gene sequences encode an antigen.

10. The rSPV of claim 9, wherein the first and/or second foreign gene sequences encode a PCV2 antigen, a PCV2 capsid antigen, or a PCV2 ORF2 protein or peptide.

11. The rSPV of claim 9, wherein each of the first and/or second foreign gene sequences contains a transcriptional promoter.

12. The rSPV of claim 11, wherein each promoter is selected from the group consisting of: a vaccinia virus 7.5-kD promoter (P7.5k), a vaccinia virus 11-kD promoter (P11k), a vaccinia virus 28-kD promoter (P28k), an artificial synthetic Poxvirus promoter (Ps), a chicken beta-actin (Bac) promoter a Pec promoter, a Murine Cytomegalovirus (Mcmv) immediate-early (ie)1 promoter, a Human Cytomegalovirus promoter (Hcmv), the Simian virus (SV)40 promoter, or a Raus Sarcoma virus (RSV) promoter.

13. The rSPV of claim 1, said rSPV comprising a first nucleic acid sequence encoding a PCV2 antigen inserted in place of the deleted TK gene sequence of the rSPV genome, and a second nucleic acid sequence encoding a PCV2 antigen inserted in place of the deleted IL18bp gene sequence of the rSPV genome.

14. A recombinant swinepox virus (rSPV) having a defective viral IL18bp gene, wherein the viral genes are defective by deletion.

15. A nucleic acid molecule comprising the genome of the rSPV of claim 1.

16. An isolated host cell comprising the rSPV of claim 1.

17. A method for producing a rSVP comprising infecting a competent cell with a nucleic acid molecule of claim 14 and collecting the rSVP.

18. A composition comprising the rSVP of claim 1 and an excipient.

19. The composition of claim 18, which is a vaccine.

20. A method of immunizing a porcine comprising administering an effective amount of the rSPV according to claim 18 to said porcine animal.

21. A vaccination kit for immunizing a porcine which comprises the following components:
a) an effective amount of the vaccine of claim 15, and
b) a means for administering said vaccine to said porcine.

22. An isolated cell comprising the nucleic acid of claim 15.

* * * * *

UNITED STATES PATENT AND TRADEMARK OFFICE
CERTIFICATE OF CORRECTION

PATENT NO. : 11,020,472 B2  
APPLICATION NO. : 16/307954  
DATED : June 1, 2021  
INVENTOR(S) : Takanori Sato, Shuji Saitoh and Yasutoshi Komiya Page 1 of 1

It is certified that error appears in the above-identified patent and that said Letters Patent is hereby corrected as shown below:

In the Specification

Column 3,
Line 13, "Ps-91." should read --pSP91.--.
Line 14, "FIG. 2," should read --FIG. 2.--.
Line 22, "FIG. 6" should read --FIG. 6.--.
Line 65, "rSPVs" should read --rSPVs.--.

In the Claims

Column 36,
Line 21, "claim 15" should read --claim 19--.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 27

<210> SEQ ID NO 1
<211> LENGTH: 22
<212> TYPE: DNA
<213> ORGANISM: Artificial
<220> FEATURE:
<223> OTHER INFORMATION: oligonucleotide

<400> SEQUENCE: 1
cgaattcatt cctttatctt ta                                             22

<210> SEQ ID NO 2
<211> LENGTH: 21
<212> TYPE: DNA
<213> ORGANISM: Artificial
<220> FEATURE:
<223> OTHER INFORMATION: oligonucleotide

<400> SEQUENCE: 2
ggaactacgt tatacgatca t                                              21
```

<210> SEQ ID NO 3
<211> LENGTH: 38
<212> TYPE: DNA
<213> ORGANISM: Artificial
<220> FEATURE:
<223> OTHER INFORMATION: oligonucleotide

<400> SEQUENCE: 3
ttcgccctta cggtaccatt cctttatctt tataaacg                             38

<210> SEQ ID NO 4
<211> LENGTH: 39
<212> TYPE: DNA
<213> ORGANISM: Artificial
<220> FEATURE:
<223> OTHER INFORMATION: oligonucleotide

<400> SEQUENCE: 4
ctataatatt aaataagctt tatggagttg tttaaatac                            39

<210> SEQ ID NO 5
<211> LENGTH: 35
<212> TYPE: DNA
<213> ORGANISM: Artificial
<220> FEATURE:
<223> OTHER INFORMATION: oligonucleotide

<400> SEQUENCE: 5
cacacgataa cactgcagtc cacatattac ggttc                                35

<210> SEQ ID NO 6
<211> LENGTH: 32
<212> TYPE: DNA
<213> ORGANISM: Artificial
<220> FEATURE:
<223> OTHER INFORMATION: oligonucleotide

<400> SEQUENCE: 6
gccgcgaatt cgccctcgag gagctcacta cg                                   32

<210> SEQ ID NO 7
<211> LENGTH: 46
<212> TYPE: DNA
<213> ORGANISM: Artificial
<220> FEATURE:
<223> OTHER INFORMATION: oligonucleotide

<400> SEQUENCE: 7
aattgcccgg gtaccgtcga tcgactttt atggcccccc cggcca                     46

<210> SEQ ID NO 8
<211> LENGTH: 46
<212> TYPE: DNA
<213> ORGANISM: Artificial
<220> FEATURE:
<223> OTHER INFORMATION: oligonucleotide

<400> SEQUENCE: 8
agcttggccg ggggggccat aaaaagtcga tcgacggtac ccgggc                    46

<210> SEQ ID NO 9
<211> LENGTH: 103
<212> TYPE: DNA
<213> ORGANISM: Artificial
<220> FEATURE:

<223> OTHER INFORMATION: oligonucleotide

<400> SEQUENCE: 9

| | | |
|---|---|---|
| ggtaccgagc tcggtagccc gggccatggt agatcctcta gaggatccaa ttcatttata | 60 |
| gcatagaaaa aaacaaaatg aaattctact atattttctg cag | 103 |

<210> SEQ ID NO 10
<211> LENGTH: 702
<212> TYPE: DNA
<213> ORGANISM: Artificial
<220> FEATURE:
<223> OTHER INFORMATION: synthetic ORF2

<400> SEQUENCE: 10

| | |
|---|---|
| atgacctacc ctagaagaag atataggagg cggaggcatc ggccacggag tcacctggga | 60 |
| caaattctgc ggagaaggcc atggttggtg catccaagac atagatatag gtggaggaga | 120 |
| aagaacggaa tctttaatac aagactgtct agaactttg gtacaccgt gaaaagaaca | 180 |
| accgtgagga ccccatcttg gccgttgat atgatgaggt taacatcaa cgatttcttc | 240 |
| cctcctgggg gaggatctaa tcctagatcc gttccattcg agtattatag gatcaggaaa | 300 |
| gtgaaagtgg agttttggcc atgtagccca attactcaag gagatagagg tgttggatct | 360 |
| agcgccgtga tcctggacga caatttcgtg accaaagcaa ccgcactgac ttacgatcct | 420 |
| tacgtgaatt attctagcag acacactatt actcaaccat ttagctatca cagcagatat | 480 |
| ttcactccta agccagtgct ggacagcacc atcgactatt ttcagcctaa taataagagg | 540 |
| aatcaacttt ggcttaggct tcagaccgcc gggaacgtgg atcacgtggg attgggaacc | 600 |
| gcatttgaga attctatttta tgatcaagag tataacatta gagtgactat gtacgtgcag | 660 |
| tttagggagt caacctgaa agatccacct ctgaatccat aa | 702 |

<210> SEQ ID NO 11
<211> LENGTH: 702
<212> TYPE: DNA
<213> ORGANISM: Artificial
<220> FEATURE:
<223> OTHER INFORMATION: synthetic ORF2

<400> SEQUENCE: 11

| | |
|---|---|
| atgaaaacga tttccgttgt tacgttgtta tgcgtactac ctgctgttgt ttattcaaca | 60 |
| tgtactgtac ccactatgaa taacgctaaa ttgacgtcta ccgaaacatc gtggaaaaaa | 120 |
| gagaaaggag tcttgaacac cagattgtct agaaccttcg gttacaccat taagagaacc | 180 |
| accgtcaaaa cccccatcttg ggctgtcgat atgatgagat tcaacatcaa cgatttcgtc | 240 |
| ccacctggtg gtggatcaaa ccctagatcc gttccattcg agtactacag aatcagaaaa | 300 |
| gtcaaagtcg agttctggcc atgctctcct attactcagg gtgatagagg agttggatca | 360 |
| actgccgtca tcttggatga caacttcgtc actaaggcta ctgccttgac ctacgatcct | 420 |
| tacgtcaatt actctagtag acacaccatc acccaaccat tctcatacca ttccagatac | 480 |
| ttcactccaa aacctgtctt ggactcaacc atcgattact tcaaccaaa caacaagaga | 540 |
| aaccaattgt ggttgagatt gcaaactgcc ggtaacgtcg atcatgtcgg attgggaacc | 600 |
| gccttcgaaa actccaaata cgaccaggag tacaacatta gagtcaccat gtacgtccaa | 660 |
| ttcagagagt caacttgaa ggacccacca ttgaacccat aa | 702 |

<210> SEQ ID NO 12
<211> LENGTH: 288

```
<212> TYPE: DNA
<213> ORGANISM: Artificial
<220> FEATURE:
<223> OTHER INFORMATION: oligonucleotide

<400> SEQUENCE: 12
aagcttggcc gggggggcca gctcggtaca taaaaatgtc gacggatccg agtgcaataa    60
attagaatag tttttcaatt tttacgcgta attaattatt gtatttatta tttatatgcc   120
aaaaaaaaaa aaaaaaaaaa gcttcataaa aagtcgatcg acggtaccac ccggggatcg   180
atccaaaaaa atctttcggc ctgcatgaat ggccttgttg atcgcttatt attattttg    240
acaccagacc aactggtaat ggtagcgacc ggcgctcagc tggaattc                288

<210> SEQ ID NO 13
<211> LENGTH: 714
<212> TYPE: DNA
<213> ORGANISM: Artificial
<220> FEATURE:
<223> OTHER INFORMATION: synthetic ORF2

<400> SEQUENCE: 13
ggatccatga cgtatccaag gaggcgttac cgcagaagaa gacaccgccc ccgcagccat    60
cttggccaga tcctccgccg ccgccccctgg ctcgtccacc ccgccaccg ctaccgttgg   120
agaaggaaaa atggcatctt caacacccgc ctctcccgca ccttcggata tactgtcaag   180
cgtaccacgg tcacaacgcc ctcctgggcg gtggacatga tgagatttaa acttgacgac   240
tttgttcccc cgggaggggg gaccaacaaa atctctatac cctttgaata ctacagaata   300
agaaaggtta aggttgaatt ctggccctgc tcccccatca cccagggtga taggggagtg   360
ggctccactg ctgttattct agatgataac tttgtaccaa aggcaccagc cctaaccctat   420
gacccatatg taaactactc ctcccgccat acaatccccc aacccttctc ctaccactcc   480
cgttacttca cacccaaacc tgttcttgac tccactattg attacttcca accaaataac   540
aaaaggaatc agctttggct gaggctacaa acctctagaa atgtggacca cgtaggcctc   600
ggcactgcgt tcgaaaacag taaatacgac caagactaca atatccgtgt aaccatgtat   660
gtacaattca gagaatttaa tcttaaagac cccccactta acccctaagt cgac          714

<210> SEQ ID NO 14
<211> LENGTH: 19
<212> TYPE: DNA
<213> ORGANISM: Artificial
<220> FEATURE:
<223> OTHER INFORMATION: oligonucleotide

<400> SEQUENCE: 14
aatattacgg gtgctgttt                                                  19

<210> SEQ ID NO 15
<211> LENGTH: 18
<212> TYPE: DNA
<213> ORGANISM: Artificial
<220> FEATURE:
<223> OTHER INFORMATION: oligonucleotide

<400> SEQUENCE: 15
aaaaacatcg tattcctg                                                   18

<210> SEQ ID NO 16
<211> LENGTH: 30
<212> TYPE: DNA
```

```
<213> ORGANISM: Artificial
<220> FEATURE:
<223> OTHER INFORMATION: oligonucleotide

<400> SEQUENCE: 16
cgttcatgtt aagcttaacc tgaaatattg                                    30

<210> SEQ ID NO 17
<211> LENGTH: 33
<212> TYPE: DNA
<213> ORGANISM: Artificial
<220> FEATURE:
<223> OTHER INFORMATION: oligonucleotide

<400> SEQUENCE: 17
gtttaaacga attcggtacc cttaaaaaca tcg                                33

<210> SEQ ID NO 18
<211> LENGTH: 36
<212> TYPE: DNA
<213> ORGANISM: Artificial
<220> FEATURE:
<223> OTHER INFORMATION: oligonucleotide

<400> SEQUENCE: 18
cgccgagctc gagaatatta cgggtgctgt ttttac                             36

<210> SEQ ID NO 19
<211> LENGTH: 33
<212> TYPE: DNA
<213> ORGANISM: Artificial
<220> FEATURE:
<223> OTHER INFORMATION: oligonucleotide

<400> SEQUENCE: 19
ccagactgca gagaacatag gtcctaatat aag                                33

<210> SEQ ID NO 20
<211> LENGTH: 20
<212> TYPE: DNA
<213> ORGANISM: Artificial
<220> FEATURE:
<223> OTHER INFORMATION: oligonucleotide

<400> SEQUENCE: 20
aagtggagtt ttggccatgt                                               20

<210> SEQ ID NO 21
<211> LENGTH: 20
<212> TYPE: DNA
<213> ORGANISM: Artificial
<220> FEATURE:
<223> OTHER INFORMATION: oligonucleotide

<400> SEQUENCE: 21
tccagcactg gcttaggagt                                               20

<210> SEQ ID NO 22
<211> LENGTH: 24
<212> TYPE: DNA
<213> ORGANISM: Artificial
<220> FEATURE:
<223> OTHER INFORMATION: oligonucleotide

<400> SEQUENCE: 22
caattgaaac atctatatat cctt                                          24
```

```
<210> SEQ ID NO 23
<211> LENGTH: 23
<212> TYPE: DNA
<213> ORGANISM: Artificial
<220> FEATURE:
<223> OTHER INFORMATION: oligonucleotide

<400> SEQUENCE: 23
caatgtgaag cgataaaata cag                                          23

<210> SEQ ID NO 24
<211> LENGTH: 20
<212> TYPE: DNA
<213> ORGANISM: Artificial
<220> FEATURE:
<223> OTHER INFORMATION: oligonucleotide

<400> SEQUENCE: 24
tatgtctaaa ggtgcgtcta                                              20

<210> SEQ ID NO 25
<211> LENGTH: 21
<212> TYPE: DNA
<213> ORGANISM: Artificial
<220> FEATURE:
<223> OTHER INFORMATION: oligonucleotide

<400> SEQUENCE: 25
agtggctata ttatcatcct g                                            21

<210> SEQ ID NO 26
<211> LENGTH: 22
<212> TYPE: DNA
<213> ORGANISM: Artificial
<220> FEATURE:
<223> OTHER INFORMATION: oligonucleotide

<400> SEQUENCE: 26
atacgattaa gcgatagtga ta                                           22

<210> SEQ ID NO 27
<211> LENGTH: 23
<212> TYPE: DNA
<213> ORGANISM: Artificial
<220> FEATURE:
<223> OTHER INFORMATION: oligonucleotide

<400> SEQUENCE: 27
atattatttt catttgtttc cta                                          23
```